(12) United States Patent
Marshall

(10) Patent No.: US 10,441,261 B2
(45) Date of Patent: Oct. 15, 2019

(54) TISSUE CLOSING METHOD AND APPARATUS

(71) Applicant: Roffe Medical Holdings Pty Ltd, Robina, Queensland (AU)

(72) Inventor: Kevin Marshall, Robina (AU)

(73) Assignee: ROFFE MEDICAL HOLDINGS PTY LTD., Robina, Queensland (AU)

( * ) Notice: Subject to any disclaimer, the term of this patent is extended or adjusted under 35 U.S.C. 154(b) by 155 days.

(21) Appl. No.: 15/507,211

(22) PCT Filed: Apr. 28, 2015

(86) PCT No.: PCT/AU2015/050201
§ 371 (c)(1),
(2) Date: Feb. 27, 2017

(87) PCT Pub. No.: WO2015/164923
PCT Pub. Date: Nov. 5, 2015

(65) Prior Publication Data
US 2017/0296161 A1    Oct. 19, 2017

Related U.S. Application Data

(60) Provisional application No. 61/986,042, filed on Apr. 29, 2014.

(30) Foreign Application Priority Data

Nov. 5, 2014  (AU) ................................ 2014904442

(51) Int. Cl.
*A61B 17/02*  (2006.01)
*A61B 17/08*  (2006.01)
(Continued)

(52) U.S. Cl.
CPC .......... *A61B 17/0218* (2013.01); *A61B 17/02* (2013.01); *A61B 17/08* (2013.01);
(Continued)

(58) Field of Classification Search
CPC .............. A61B 17/0218; A61B 17/085; A61B 17/32093; A61B 17/3423; A61B 90/30;
(Continued)

(56) References Cited

U.S. PATENT DOCUMENTS 3,926,193 A    12/1975  Hasson
4,430,998 A    2/1984   Harvey et al.
(Continued)

FOREIGN PATENT DOCUMENTS

CA    2 770 834 C    2/2011
CN    103705283 A   4/2014
(Continued)

*Primary Examiner* — Pedro Philogene
*Assistant Examiner* — David C Comstock
(74) *Attorney, Agent, or Firm* — Knobbe Martens Olson & Bear, LLP

(57) ABSTRACT

An apparatus for opening or closing a tissue opening in a biological subject, the apparatus including at least two flexible arms coupled to a tissue surface in use, each arm being curved outwardly in a mid-portion to accommodate a tissue opening therebetween and a biasing mechanism that selectively biases opposing ends of each arm to thereby at least one of bias mid-portions of the arms apart to assist in at least partially opening the tissue opening; and bias mid-portions of the arms towards each other to assist in at least partially closing the tissue opening.

20 Claims, 24 Drawing Sheets

(51) Int. Cl.
*A61B 17/3209* (2006.01)
*A61B 17/34* (2006.01)
*A61B 90/30* (2016.01)
*A61B 17/00* (2006.01)

(52) U.S. Cl.
CPC ...... *A61B 17/085* (2013.01); *A61B 17/32093* (2013.01); *A61B 17/3423* (2013.01); *A61B 90/30* (2016.02); *A61B 2017/00893* (2013.01); *A61B 2017/0225* (2013.01); *A61B 2017/0287* (2013.01); *A61B 2017/081* (2013.01)

(58) Field of Classification Search
CPC .. A61B 2017/00893; A61B 2017/0225; A61B 2017/0287; A61B 2017/081
USPC ............ 602/41, 42, 43, 52, 53, 54; 600/206, 600/208, 210
See application file for complete search history.

(56) References Cited

U.S. PATENT DOCUMENTS

| | | | |
|---|---|---|---|
| 6,126,615 A | 10/2000 | Allen et al. | |
| 7,429,265 B2 | 9/2008 | O'Malley et al. | |
| 8,063,263 B2* | 11/2011 | Gurtner ................. | A61K 47/67 523/111 |
| 8,313,508 B2 | 11/2012 | Belson et al. | |
| 9,179,914 B2* | 11/2015 | Belson ................... | A61B 17/08 |
| 9,241,835 B2 | 1/2016 | Zepeda et al. | |
| 9,358,009 B2 | 6/2016 | Yock et al. | |
| 9,463,020 B2 | 10/2016 | Wilke et al. | |
| 9,668,922 B2 | 6/2017 | Zepeda et al. | |
| 9,827,447 B1 | 11/2017 | Levi et al. | |
| 9,844,470 B2 | 12/2017 | Jackson et al. | |
| 10,213,350 B2 | 2/2019 | Jackson et al. | |
| 2003/0163160 A1 | 8/2003 | O'Malley et al. | |
| 2007/0088339 A1* | 4/2007 | Luchetti ............... | A61B 17/085 606/1 |
| 2009/0177227 A1 | 7/2009 | Warren | |
| 2010/0100022 A1* | 4/2010 | Greener ............... | A61B 17/083 602/44 |
| 2011/0276089 A1 | 11/2011 | Strachnz et al. | |
| 2012/0046590 A1 | 2/2012 | Yock et al. | |
| 2013/0066365 A1 | 3/2013 | Belson et al. | |
| 2013/0110026 A1 | 5/2013 | Jackson et al. | |
| 2013/0190655 A1 | 7/2013 | Jackson et al. | |
| 2013/0281904 A1 | 10/2013 | Jackson et al. | |
| 2013/0296930 A1 | 11/2013 | Belson et al. | |
| 2014/0074156 A1 | 3/2014 | Belson et al. | |
| 2014/0088643 A1 | 3/2014 | Wilke et al. | |
| 2014/0200409 A1* | 7/2014 | Green ...................... | A61B 1/32 600/208 |
| 2016/0022504 A1* | 1/2016 | Goldman ........... | A61B 17/1325 602/44 |

FOREIGN PATENT DOCUMENTS

| | | |
|---|---|---|
| DE | 10 2007 011 570 A1 | 9/2008 |
| EP | 2 680 800 B1 | 4/2016 |
| EP | 2 811 956 B1 | 8/2017 |
| JP | S58 191007 U | 12/1983 |
| KR | 20150130527 A | 11/2015 |
| RU | 2 238 683 C2 | 10/2004 |
| WO | WO 2009/066116 A1 | 5/2009 |
| WO | WO 2013/038182 A2 | 3/2013 |
| WO | WO 2013/071439 A1 | 5/2013 |

* cited by examiner

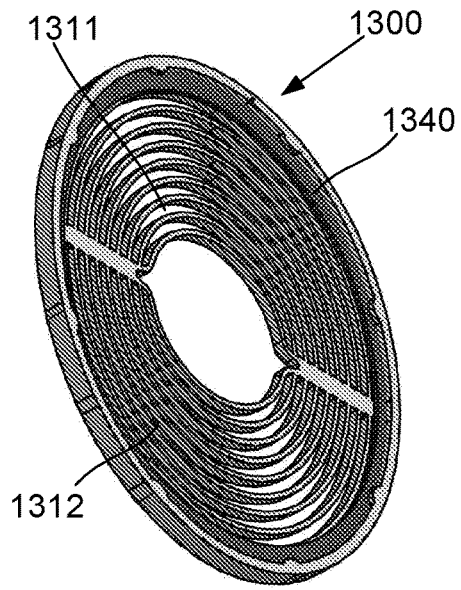
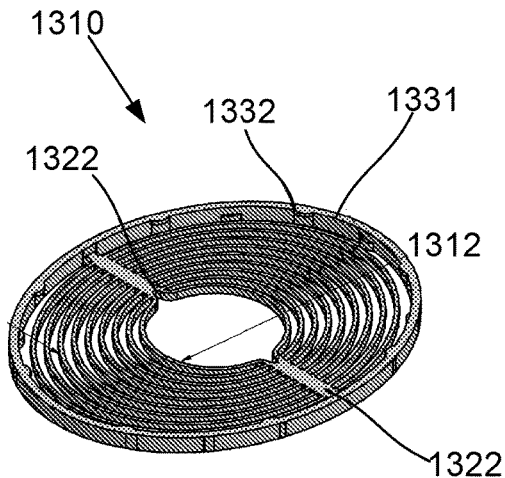
Fig. 13A  Fig. 13B
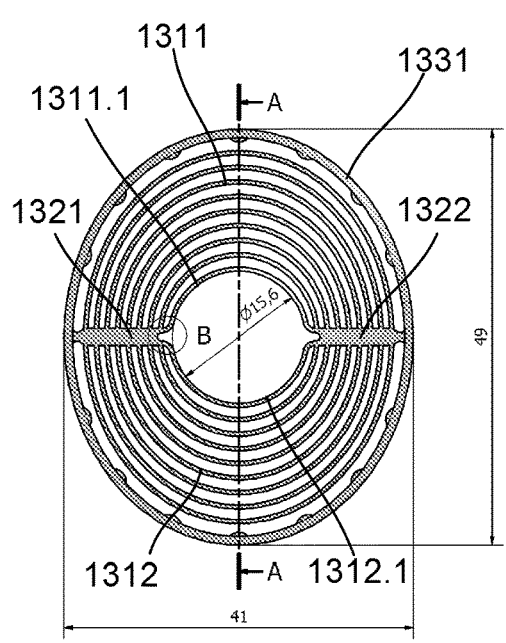
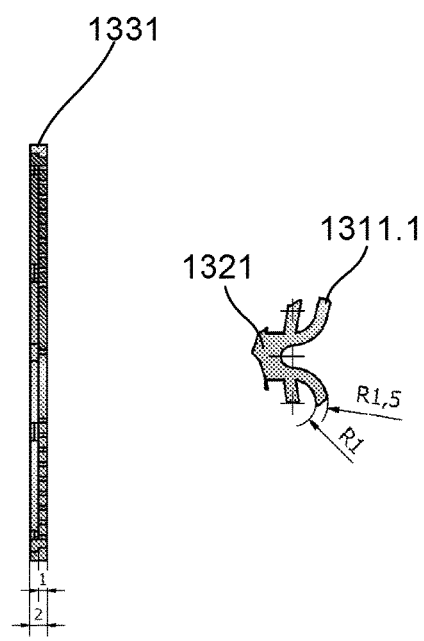
Fig. 13C  Fig. 13D  Fig. 13E

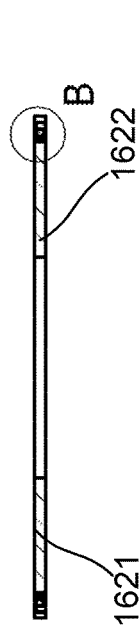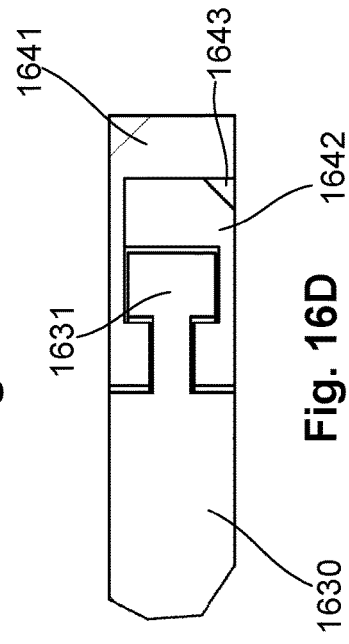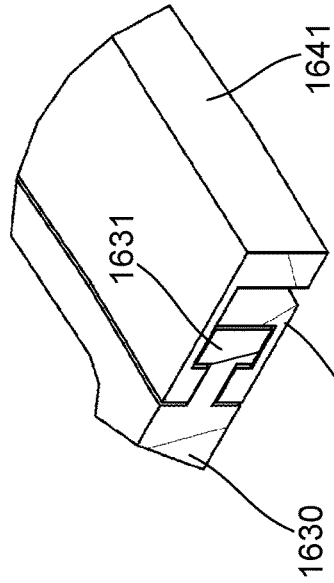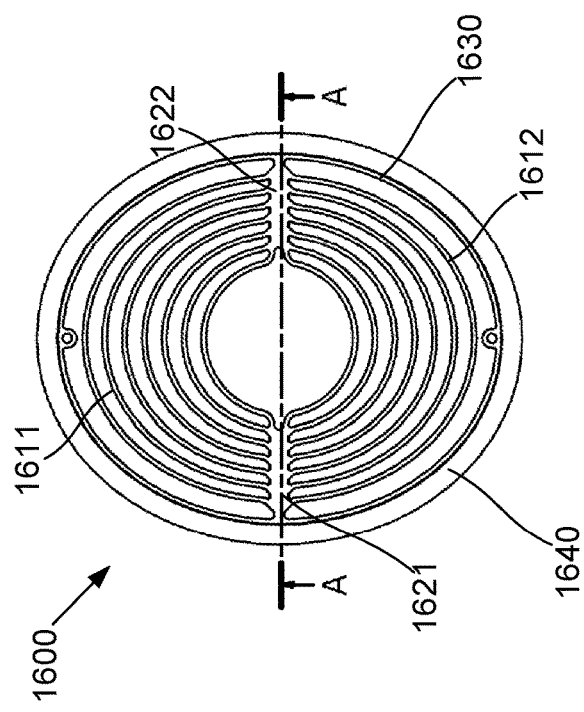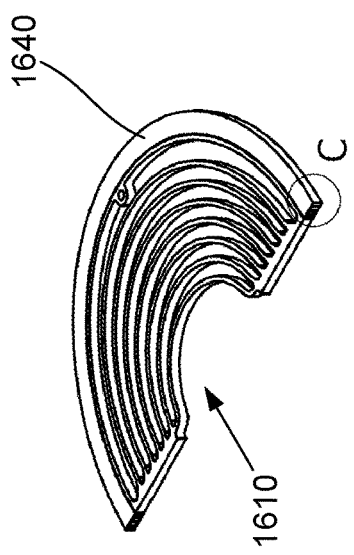

TISSUE CLOSING METHOD AND APPARATUS

BACKGROUND OF THE INVENTION

The present invention relates to a method and apparatus for closing a tissue opening and also a method and apparatus for opening and closing a tissue opening.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to provide a range of different mechanisms for closing tissue openings, such as wounds and surgical incisions. This can include adhesive plasters or bandages, which are placed over the wound. Whilst easy to apply, these typically only operate to protect the wound, and optionally apply some pressure to the wound, but generally are unsuitable for major wounds. They also only have limited capabilities to prevent the wound reopening in the event that the tissue is stretched, and typically obstruct air flow to the wound, which can hamper the healing process.

As an alternative stitches or sutures may be used. These operate by extending across the tissue opening and are used to draw edges of the wound together. This can prevent the wound re-opening if the wound is stretched and are more suitable for major wounds. However, these suffer from a number of disadvantages, including that they can generally only be applied by a trained individual, their application, use and removal can be unpleasant, and they tend to interfere with the wound opening, which can cause infection, irritation and discomfort. A further issue is that forces on the tissue tend to be localised, which can in turn be problematic in the case of weakened tissue, which may arise in the event of tissue necrosis or the like around the wound, which can cause wound dehiscence, tissue rupture or the like.

U.S. Pat. No. 8,313,508 describes a biopsy incision closure device that includes a base having a frame incorporated therein. Together, the base and frame define an opening for performing a biopsy incision when the device is placed over a tissue surface. The base is typically composed of an elastomeric material and the frame comprises resilient inelastic members which can be used to close the opening in a highly uniform manner with minimum distortion and stress introduced into the tissue edges being drawn together. However, this requires a closing member that extends across the wound opening, which can cause discomfort, or irritation, as well as hindering access to the wound.

U.S. Pat. No. 7,429,265 provides a system and method of moving and stretching plastic tissue using dynamic force. An elastomeric driver is adjustably attachable to one or more anchors for securing the elastomer to the plastic tissue, providing a self adjusting system that is capable of exerting relatively constant tension over a certain distance. However, this uses tissue anchors to engage the tissue, which results in localised forces on the tissue, which is undesirable, as well as requiring a tensioning member to extend across the wound.

US2014/0088643 describes a wound closure system and a method of closing a wound, which uses a plurality of skin anchors mechanically attached to external skin tissue around a periphery of a wound, a line extending between the skin anchors, the line slidably engaged with each skin anchor, and a biasing member that provides tension on the line to draw all of the skin anchors toward the wound. The method of closing a wound includes the steps of attaching a plurality of skin anchors to external skin around a periphery of a wound, extending a line between the skin anchors around substantially the entire periphery of the wound, and providing tension to the line to draw the skin anchors toward the wound. However, this again uses skin anchors, which places localised pressure on the skin, and hence is undesirable.

US2011/0276089 describes an incision guide and wound closure device including a surgical mesh having a top surface and a bottom surface, and first and second incision guides affixed to the top surface of the surgical mesh. The bottom surface of the mesh is adhered to tissue using clear or translucent adhesive. The first and second incision guides have opposing alignment surfaces that are adapted to guide a cutting instrument for making an incision through the mesh and into the tissue. The device has a closing element that is moveable along the length of the respective first and second incision guides for drawing the first and second alignment surfaces toward one another for closing the incision opening in the tissue. However, this uses a slidable guide similar to a zipper, which draws the surgical mesh over the wound, thereby preventing access and airflow to the wound, which hampers healing and can cause wound irritation.

WO2013/038182 describes a method of closing a wound with a dressing. The method including: restraining at least a portion of the dressing corresponding to the wound into a first shape; adhering first and second portions of the dressing across the wound; removing the restraint from the dressing while the first and second portions are adhered to the skin by removing a member from the dressing to allow at least the portion to move towards a second shape and apply a force tending to close the wound. This utilises a spring based mechanism that extend across the wound to draw edges of the wound together. However, this provides limited control of the force applied to the wound and also requires the tensioning member extend across the wound, which can in turn interfere with and irritate the wound.

SUMMARY OF THE PRESENT INVENTION

In one broad form the invention seeks to provide apparatus for closing a tissue opening in a biological subject, the apparatus including:
 a) at least two flexible arms;
 b) a coupling mechanism that couples the arms to a tissue surface on either side of the tissue opening with each arm being curved outwardly in a mid-portion to thereby accommodate the tissue opening therebetween;
 c) a biasing mechanism for biasing opposing ends of each arm apart to thereby at least partially straighten the arms, which in turn biases the mid-portions towards each other to at least partially close the tissue opening.

Typically the at least two arms are provided laterally on either side of the tissue opening and wherein the biasing mechanism biases ends of the arms longitudinally relative to the opening.

Typically the biasing mechanism moves ends of the arms:
 a) together so as to increase curvature of the arms to thereby bias mid-portions of the arms apart to assist in at least partially opening the tissue opening; and, b) apart so as to at least partially straighten the arms to thereby bias mid-portions of the arms towards each other to assist in at least partially closing the tissue opening.

Typically the apparatus includes a plurality of laterally spaced first arms on a first side of the tissue opening and a plurality of laterally spaced second arms on a second side of the tissue opening.

Typically at least mid-portions of the first and second arms are curved outwardly in an unbiased state, and wherein the radius of curvature is greater for arms further away from the tissue opening.

Typically first and second arms further away from the tissue opening have a greater length.

Typically mid-portions of the arms are spaced further apart away from the tissue opening.

Typically adjusting a separation of the opposing ends of each arm causes a progressively smaller degree of lateral movement of the mid portion a greater distance away from the tissue opening to thereby distribute tension through the tissue surface.

Typically the apparatus includes a membrane extending between at least some of the first arms and between at least some of the second arms.

Typically the arms are at least one of:
a) coupled to the membrane; and,
b) integrally formed with the membrane.

Typically the membrane provides a contact surface for coupling the apparatus to the subject.

Typically the arms are coupled to a frame and wherein the biasing mechanism at least partially deforms the frame to thereby bias opposing ends of each arm.

Typically the biasing mechanism includes a drive ring that engages the frame, and wherein the frame and drive ring are configured to deform the frame upon relative rotation of the frame and drive ring.

Typically the frame is elastically deformable.

Typically a degree of rotation adjusts an amount of biasing of the arms.

Typically the drive ring and frame are complementarily shaped.

Typically the drive ring and frame are elliptical.

Typically the drive ring is mounted at least one of:
a) inwardly of the frame; and,
b) outwardly of the frame.

Typically the frame includes a lip extending circumferentially around at least part of a perimeter of the frame and wherein the drive ring engages the lip.

Typically the drive ring is coupled to the frame using a tongue and groove arrangement.

Typically the arms are coupled to the frame via a membrane.

Typically at least one of the frame and a drive ring at least partially immobilise tissue within a perimeter of the frame.

Typically the apparatus includes an actuator including a key coupled to a handle, and wherein in use the key engages the drive ring so that rotation of the handle causes corresponding rotation of the drive ring relative to the frame.

Typically, in use, at least one tool can be selectively coupled to the drive ring to thereby support the at least one tool relative to the apparatus.

Typically, the tool includes at least one of:
a) an optical system for viewing the tissue opening;
b) a blade for creating an incision; and,
c) a guide for guiding a surgical instrument.

Typically the tool includes:
a) a tool holder including a tool holder body defining an opening; and,
b) a tool body that in use is positioned at least partially within the tool holder body.

Typically the tool holder body forms an actuator for rotating the drive ring.

Typically the tool includes a blade and button movably mounted to the tool body to allow the blade to be deployed upon depression of the button.

Typically the arms are coupled to the frame via respective arm end portions, and wherein each arm is connected to the arm end portion via a live hinge.

Typically the arms are arranged along either side of the tissue opening so that when biased in a longitudinal direction relative to the tissue opening, the arms apply a lateral closing force to the tissue to thereby close the tissue opening.

Typically the arms are resilient and are curved in an unbiased state.

Typically the curve is at least one of:
a) in a plane;
b) substantially bell shaped; and,
c) a cubic planar curve.

Typically arms are at least one of:
a) resilient;
b) incompressible; and,
c) unstretchable.

Typically arms include at least one of:
a) a biocompatible material;
b) a core with a biocompatible coating;
c) a polymer;
d) high density polyethylene;
e) polypropylene; and,
f) metal.

Typically the apparatus is substantially planar and is deformable from a planar shape.

Typically the coupling mechanism includes at least one of:
a) an adhesive surface provided on an underside of the arms;
b) an adhesive layer provided on an underside of the arms;
c) a number of projections extending from an underside of the arms, the projections penetrating the tissue surface in use; and,
d) at least one adhesive patch applied over an upperside of the arms.

Typically the biasing mechanism is adjustable to allow closing forces on the tissue opening to be controlled.

Typically a first end of each arm is coupled to a first arm end portion and a second end of each arm is coupled of to a second arm end portion and wherein a relative separation of the first and second arm end portions provides the biasing mechanism.

Typically the first and second arm end portions are coupled to the tissue surface in use.

Typically the first and second arm end portions are coupled to the tissue surface by at least one of:
a) an adhesive surface provided on an underside of the arm end portions;
b) an adhesive layer provided on an underside of the arm end portions;
c) a number of projections extending from an underside of the arm end portions, the projections penetrating the tissue surface in use; and,
d) at least one adhesive patch applied over an upperside of the arm end portions.

Typically the apparatus is adhesive and the apparatus includes one or more releasable layers.

Typically the apparatus includes separate releasable layers on the arms and on arm end portions.

Typically the apparatus includes a plurality of laterally spaced first arms on a first side of the tissue opening and a plurality of laterally spaced second arms on a second side of the tissue opening.

Typically at least mid-portions of the first and second arms are curved outwardly in an unbiased state, and wherein the radius of curvature is greater for arms further away from the tissue opening.

Typically first and second arms further away from the tissue opening have a greater length.

Typically mid-portions of the arms are spaced further apart away from the tissue opening.

Typically biasing of the first and second arms causes a progressively smaller degree of lateral movement further away from the tissue opening.

Typically the degree of movement distributes tension through the tissue surface.

Typically the apparatus includes at least one biasing member extending between the arm end portions to bias the arm end portions.

Typically the at least one biasing member is telescopic.

Typically the at least one biasing member is adjustably coupled to at least one of the arm end portions after the arm end portions are biased apart.

Typically at least one of first and second arm end portions are coupled to a frame.

Typically the frame at least one of:
a) extends around at least part of a perimeter of the apparatus; and,
b) surrounds at least part of the arms and arm end portions.

Typically the frame is coupled to the tissue surface.

Typically the frame is coupled to the tissue surface by at least one of:
a) an adhesive surface provided on an underside of the arm end portions; and,
b) an adhesive layer provided on an underside of the arm end portions.

Typically a first arm end portion is coupled to the frame and a second arm end portion is movable relative to the frame so that movement of the second arm end portion provides the biasing mechanism.

Typically the second arm end portion is selectively secured to the frame using a releasable fastener.

Typically the apparatus includes a threaded member coupled to the second arm end portion and the frame so that rotation of the threaded member adjusts a separation of the second arm end portion and the frame.

Typically the threaded member includes at least one of a universal joint and flexible torque transmission system.

Typically the arms have at least one of:
a) a substantially rectangular cross section; and,
b) a flattened underside.

Typically biasing of the arms generates a torsional force in the mid-portions of the arms, and wherein the torsional force results in a downward force on the tissue surface.

Typically arms include projections that extend from an underside of the arms and penetrate the tissue surface in use and wherein at least one of:
a) the projections are adapted to the deliver a bioactive material into the tissue around the tissue opening; and,
b) the projections generate a closing force in the dermal layers below the tissue surface thereby closing the tissue opening below the tissue surface.

In one broad form the invention seeks to provide a method of closing a tissue opening in a biological subject, the method including:
a) coupling at least two flexible arms to a tissue surface on either side of the tissue opening with each arm being curved outwardly in a mid-portion to thereby accommodate the tissue opening therebetween; and,
b) biasing opposing ends of each arm apart to thereby at least partially straighten the arms, which in turn biases the mid-portions towards each other to at least partially close the tissue opening.

Typically the method includes:
a) removing a releasable layer from at least the arms;
b) adhering the arms to the tissue on either side of the tissue opening;
c) removing a releasable layer from arm end portions at either end of the arms;
d) pulling the arm end portions apart; and,
e) adhering the arm end portions to the tissue.

Typically the method includes:
a) applying a frame and arms to tissue surrounding a tissue opening;
b) adjusting a position of an arm end portion relative to the frame to thereby bias opposing ends of each arm apart.

Typically the method includes:
a) coupling arms to a tissue surface;
b) at least partially biasing the arms;
c) creating an incision between the arms; and,
d) at least partially unbiasing the arms so that the mid-portions move apart to thereby open the incision and create a tissue opening.

In one broad form the invention seeks to provide apparatus for opening and closing a tissue opening in a biological subject, the apparatus including:
a) at least two flexible arms;
b) a coupling mechanism that couples the arms to a tissue surface, wherein each arm is curved outwardly in a mid-portion to thereby provide an opening therebetween;
c) a biasing mechanism for selectively biasing opposing ends of each arm apart to thereby at least one of:
i) increase curvature of the arms to thereby bias mid-portions of the arms apart to assist in at least partially opening the tissue opening; and,
ii) at least partially straighten the arms to thereby bias mid-portions of the arms towards each other to assist in at least partially closing the tissue opening.

In one broad form the invention seeks to provide a method of creating a tissue opening in a biological subject, the method including:
a) coupling at least two flexible arms to a tissue surface, wherein in an unbiased state the arms are resilient and curved in at least a mid-portion;
b) at least partially biasing opposing ends of each arm apart so that the arms are at least partially straightened;
c) creating an incision between the arms; and,
d) at least partially biasing the opposing ends of the arms so that the mid-portions move apart to thereby open the incision and create a tissue opening.

In one broad form the invention seeks to provide apparatus for closing a tissue opening in a biological subject, the apparatus including:
a) at least two flexible arms;
b) a coupling mechanism that couples the arms to a tissue surface on either side of the tissue opening with each arm being curved outwardly in a mid-portion to thereby accommodate the tissue opening therebetween;

c) a biasing mechanism for biasing opposing ends of each arm apart to thereby at least partially straighten the arms, which in turn biases the mid-portions towards each other to at least partially close the tissue opening.

It will be appreciated that the broad forms of the invention can be used independently or in conjunction, depending on the preferred implementation and that features of the method can be performed by the method and vice versa.

BRIEF DESCRIPTION OF THE DRAWINGS

An example of the present invention will now be described with reference to the accompanying drawings, in which:—

FIG. 13A is a schematic perspective view of a further example of an apparatus for use in trocar surgery;

FIG. 13B is a second schematic perspective view of the apparatus of FIG. 13A with the drive ring removed;

FIG. 13C is a schematic plan view of the apparatus of FIG. 13B in the open position;

FIG. 13D is a schematic cut through view of the apparatus of FIG. 13C;

FIG. 13E is a close up view of the live hinge of FIG. 13C;

FIG. 16A is a schematic plan view of a further example of apparatus for opening/closing a tissue opening;

FIG. 16B is a schematic perspective cut-away view of the apparatus of FIG. 16A;

FIG. 16C is a schematic cross sectional view of the apparatus of FIG. 16A;

FIG. 16D is a schematic close up cross sectional view of the drive ring coupling of the apparatus of FIG. 16A;

FIG. 16E is a schematic perspective close up cross sectional view of the drive ring coupling of the apparatus of FIG. 16A;

FIG. 1E is a schematic plan view of a second modified version of the apparatus of FIG. 17A;

DETAILED DESCRIPTION OF THE PREFERRED EMBODIMENTS

An example of an apparatus for closing a tissue opening in a biological subject will now be described with reference to FIGS. 1A to 1E.

Figure 1A:
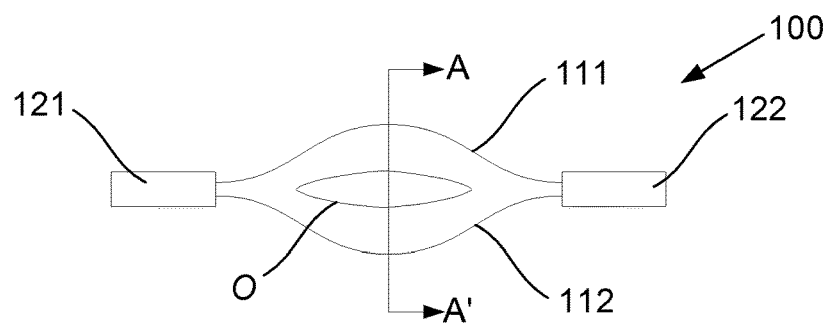
FIG. 1A is a schematic plan view of a first example of apparatus for closing a tissue opening with the apparatus in an open position.
Figure 1B:
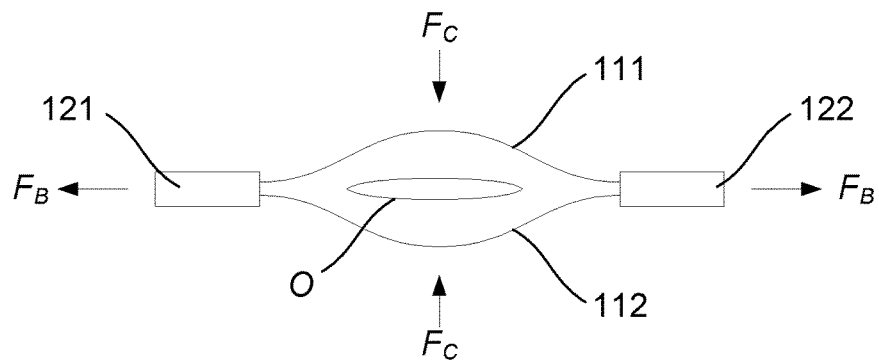
FIG. 1B is a schematic plan view of the apparatus of FIG. 1A with the apparatus in a partially closed position.
Figure 1C:
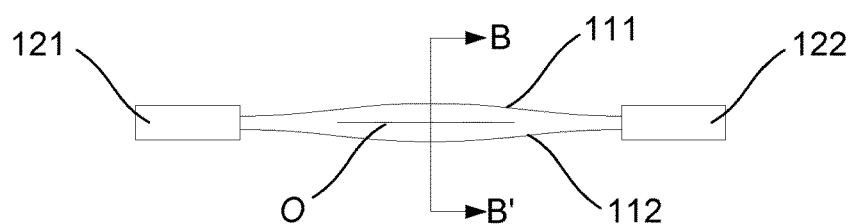
FIG. 1C is a schematic plan view of the apparatus of FIG. 1A with the apparatus in a closed position.
Figure 1D:
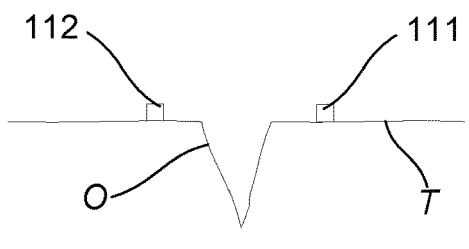
FIG. 1D is a schematic cross sectional view of the apparatus of FIG. 1A along the line A-A'.

In this example, the apparatus 100 includes flexible arms 111, 112. A coupling mechanism is provided that couples the arms 111, 112 to a tissue surface T on either side of a tissue opening O. The coupling mechanism can be of any appropriate form, such as adhesive, projections, teeth or the like, and specific examples will be described in more detail below. Each arm is curved outwardly in a mid-portion to thereby accommodate the tissue opening O therebetween, as shown in FIGS. 1A and 1D.

Figure 1E:
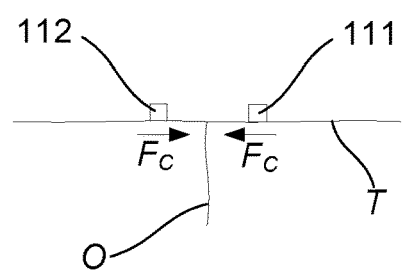
FIG. 1E is a schematic cross sectional view of the apparatus of FIG. 1C along the line B-B.

A biasing mechanism is provided for biasing opposing ends of each arm apart. The biasing mechanism can be of any appropriate form, and can include arm end portions 121, 122 that are moved apart and coupled to the tissue surface, a frame, straps, drive ring, or the like, as will be described in more detail below. In any event, the biasing mechanism applies a biasing force $F_B$ to either or both ends of each arm, thereby at least partially straighten the arms, which in turn biases the mid-portions of the arms 111, 112 towards each other. As shown in FIG. 1B, this applies a closing force $F_C$ to the tissue surface T to thereby at least partially close and more typically, fully close the tissue opening O, as shown in FIGS. 1C and 1E.

The biasing mechanism can also work in reverse, moving ends of the arms together to thereby increase arm curvature, which in turn biases the mid-portions of the arms 111, 112 apart, thereby controllably opening the tissue opening, as will be described in more detail below.

Accordingly, the above described arrangement provides a tissue closing mechanism that operates using arms that are coupled to the tissue surface, with the arms having a curved shape to accommodate a tissue opening therebetween. In use ends of each arm are biased apart to at least partially straighten the arms to apply a closing force to the tissue on either side of the tissue opening, thereby urging sides of the tissue opening together so as to close the opening.

Thus, the above described apparatus can be used to provide a method of closing a tissue opening in a biological subject simply by coupling the flexible arms 111, 112 to the tissue surface T on either side of the tissue opening O, and then biasing opposing ends of each arm 111, 112 apart to thereby at least partially straighten the arms, which in turn biases the mid-portions towards each other to at least partially close the tissue opening.

Additionally and/or alternatively, the arrangement can be used to bias ends of the arms together, to thereby open a tissue opening in a controllable manner. This can be used, to open an incision and optionally hold the incision open, for the purpose of performing surgery or the like.

This arrangement has a number of advantages over traditional wound closing mechanisms.

For example, the arrangement is relatively simple and only relies on arms that can be coupled to the tissue surface and then biased using an appropriate mechanism. This provides a cheap, simple, reliable arrangement that can be easily applied by any individual, without requiring any particular training, allowing it to be used in a wide variety of circumstances ranging from surgical procedures in a hospital, to emergency intervention situations, and home use.

Typically wounds or other tissue openings are longitudinal in nature, allowing the arms to be arranged along either side of the tissue opening so that when biased in a longitudinal direction relative to the tissue opening, the arms apply a lateral closing force to the tissue to thereby close the tissue opening. Thus, the arms extend along each side of the tissue opening so that closing forces on the tissue are evenly distributed, which avoids localised forces, thereby allowing the apparatus to be used even in situations where tissue is weakened, for example through age or infection. Furthermore, as the arms and biasing mechanism do not touch or cross over the tissue opening, this avoids irritation, whilst promoting healing through airflow. This also allows for easy inspection of the tissue opening, as well as to allow for application of medication to promote or assist healing, such as antiseptics or the like.

A further benefit is that the biasing mechanism can be adjusted to allow the magnitude of the closing force on the tissue opening to be controlled, which can in turn allow the apparatus to be used in a wide variety of circumstances, such as during exercise or sleep, whilst maximising the support provided to the tissue.

A number of further features and additional benefits will now be described in more detail.

Typically the arms are resilient and are curved in an unbiased state, as shown for example in FIG. 1A. This is not essential, and alternatively the arms could be flexible, with curvature of the arms arising from the manner in which they are coupled to the tissue. However, having naturally curved arms has a number of benefits. For example, this makes it easier to apply the apparatus, whilst also allowing the arms to return to the curved shape if biasing is reduced, which in turn can reduce the amount of closing force applied to the tissue opening. As will be described in more detail below, this can be used to assist in creating a tissue opening, for example during surgical procedures.

The curve could be of any appropriate form, but is typically in a plane and substantially bell-curve shaped. Thus in one example, the curve is in the form of a cubic planar curve, and may particularly by a cubic planar spline curve or Bezier curve. However, this is not essential and any suitable shape could be used. In particular, it will be appreciated that the curve shape will influence the closing forces $F_C$ applied along the length of the tissue opening, and accordingly, different shapes or curve profiles may be used depending on the nature of the tissue opening and/or surrounding tissue. Thus, respective profiles may be used for different applications, with custom profiles being produced for specific wounds. Additionally, the arms may be only curved along part of their length, with straight portions interconnecting the curved portions, although typically arms are curved along their entire length to ensure even distribution of closing forces on the tissue.

Additionally, suitable configuration of the curve can allow a relatively small movement of the ends of the arms 111, 112 to induce a significant displacement in the mid-portions of the arms. This ensures that undue stretching of the wound does not occur when biasing the arms.

It will be appreciated from the above that the arms are typically one or more of resilient, incompressible and unstretchable. Accordingly, the arms can have any structure and may be made of any material, that is suitable for medical applications. For example, the arms could be made of a biocompatible material or alternatively, a core with a biocompatible coating. Accordingly, the arms could be made of a polymer such as high density polyethylene, polypropylene or the like. Additionally, and/or alternatively, the arms could be made of a flexible metal such as stainless steel or the like. The apparatus could be manufactured using a variety of techniques, such as moulding, or additive manufacturing, such as 3D printing or the like, allowing custom configurations to be easily produced for specific wounds.

The nature of the coupling mechanism for attaching the arms 111, 112 to the tissue surface T will vary depending on the preferred implementation and also potentially on the application. For example a different coupling mechanism may be used depending on the degree of closing force than needs to be applied to the tissue opening. Examples of suitable coupling mechanisms include an adhesive surface provided on an underside of the arms 111, 112, an adhesive layer provided on an underside of the arms 111, 112, a number of projections extending from an underside of the arms 111, 112 so that the projections penetrate the tissue surface in use or an adhesive patch applied over an upperside of the arms 111, 112. It will also be appreciated that a combination of these coupling mechanisms can be used. For example, the arms could be adapted to adhere to the tissue surface, with an adhesive patch then being placed over the arms so that the patch adheres to the tissue surface around the arms. This can assist in retaining the arms in position, whilst also protecting the arms, to prevent them becoming dislodged, for example upon impact by an object, such as clothing worn by the subject.

The biasing mechanism is typically adjustable to allow closing forces on the tissue opening to be controlled, although this is not essential. A number of different biasing mechanisms will be described with respect to subsequent examples. However, in this example, the biasing mechanism includes first and second arm end portions 121, 122 that are coupled to the first and second ends of each arm 111, 112. In this example, the relative separation of the first and second arm end portions 121, 122 provides the biasing mechanism, with the degree of separation being used to control the biasing and hence closing force $F_C$.

The first and second arm end portions 121, 122 can be held apart using any suitable technique. In one example, the first and second arm end portions 121, 122 can be held apart by coupling them to the tissue surface using a suitable coupling mechanism, such as one or more of an adhesive surface provided on an underside of the arm end portions, an adhesive layer provided on an underside of the arm end portions, a number of projections extending from an underside of the arm end portions, the projections penetrating the tissue surface in use and at least one adhesive patch applied over an upperside of the arm end portions. Thus in this example, the arm end portions 121, 122 can act as tabs that can be grasped by a user, allowing the user to apply the biasing force $F_B$, and then couple the arm end portions 121, 122 to the tissue surface to thereby maintain the tissue opening in a closed position. However, the tabs could be secured in place using other techniques, such as straps, clips, ties or the like. Thus, for example, each arm end portion could be coupled to a strap that extends around part of the subject's body, such as a limb, or the like.

In one specific example, the apparatus of FIGS. 1A to 1E includes an adhesive layer applied to an underside of both the arms 111, 112 and the arm end portions 121, 122. In this instance, the apparatus 100 would typically be supplied with one or more releasable (peelable) layers provided on the adhesive layer, ensuring the apparatus does not inadvertently stick to objects prior to use. Such combinations of adhesive and release layers are known in the art.

For example, the adhesive layer can include ordinary pressure sensitive adhesives and may be chosen, for instance, from acrylic resins; viscous rubber compounds mainly composed of silicone rubber, polyisoprene rubber, styrene-butadiene rubber, acrylic rubber, and natural rubber; viscous vinyl compounds such as polyvinyl alcohol and ethylene-vinyl alcohol copolymer; and viscous compounds such as silicone adhesives, polyurethane elastic, polyester elastic, and polybutadiene elastic. The release or peelable layer can include one or more of a peelable paper, cellophane and synthetic resin films (polyethylene, polypropylene, polyester, polyvinylchloride, polyvinylidene chloride, and the like) having been subjected to a peeling treatment (a treatment for facilitating peeling; e.g., silicone treatment).

Figure 2:
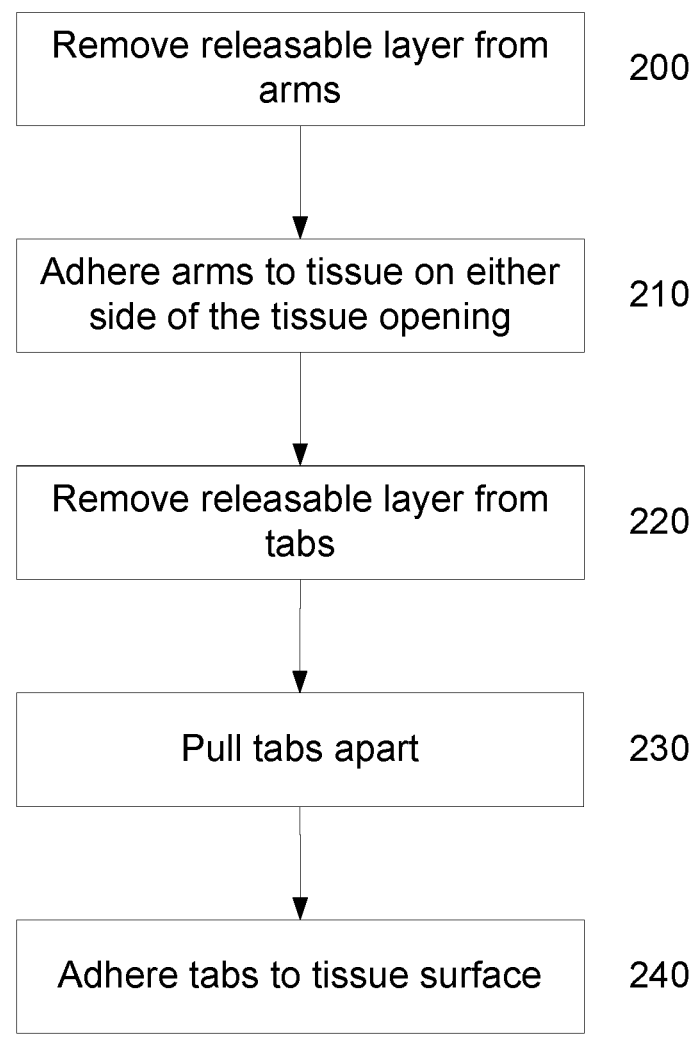
FIG. 2 is a flow chart of an example of a method for closing a tissue opening using the apparatus of FIGS. 1A to 1E.
Figure 3A:
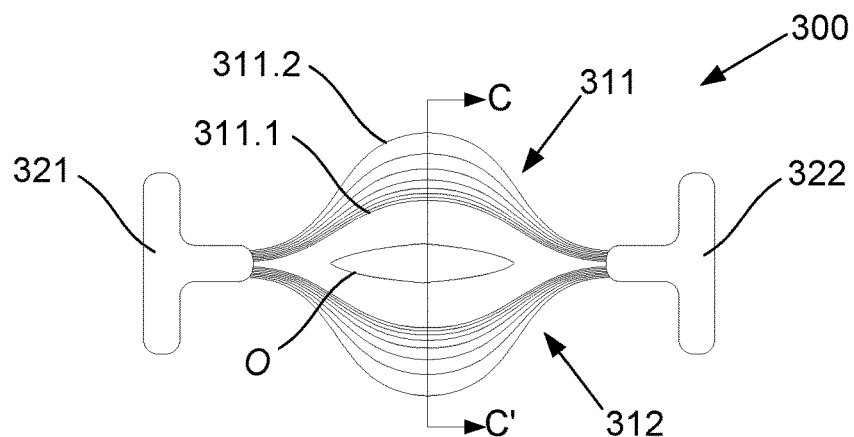
FIG. 3A is a schematic plan view of a second example of apparatus for closing a tissue opening with the apparatus in an open position.
Figure 3B:
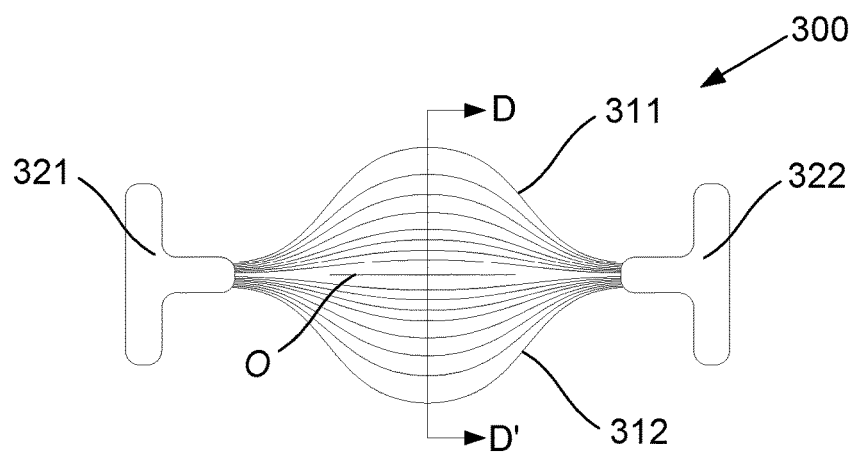
FIG. 3B is a schematic plan view of the apparatus of FIG. 3A in a closed position.
Figures 3C, 3D:
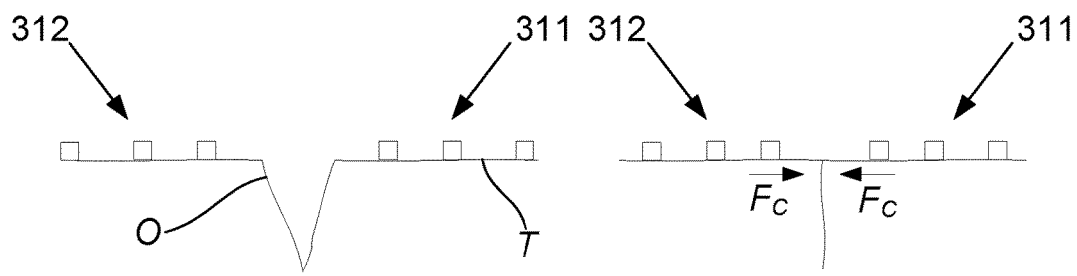
FIG. 3C is a schematic partial cross sectional view of the apparatus of FIG. 3A along the line C-C.
FIG. 3D is a schematic partial cross sectional view of the apparatus of FIG. 3C along the line D-D'.

In one specific example, the apparatus 100 includes separate releasable layers on the arms 111, 112 and on the arm end portions, which in this example are functioning as adhesive tabs. In this example, a method of applying the apparatus 100 and using this to close a tissue opening would be as shown in FIG. 2.

In particular, at step 200, the releasable layer would be removed from the arms 111, 112, with these then being adhered to the tissue on either side of the tissue opening at step 210. During this process, releasable layers can be left in place on the tabs 121, 122 so that these do not adhere to the tissue. At step 220, the releasable layers are removed from the tabs 121, 122, allowing the user to pull the tabs 121, 122 apart at step 230 and then adhere these to the tissue at step 240.

Thus, it will be appreciated that this provides a simple mechanism for applying the apparatus 100, enabling this to be used as a substitute for a standard adhesive plaster or other basic wound dressing.

A second example of an apparatus for closing a tissue opening will now be described with reference to FIGS. 3A to 3D.

In this example, the apparatus 300 includes a plurality of laterally spaced first arms 311 on a first side of the tissue opening O and a plurality of laterally spaced second arms 312 on a second side of the tissue opening O.

Figure 4A:
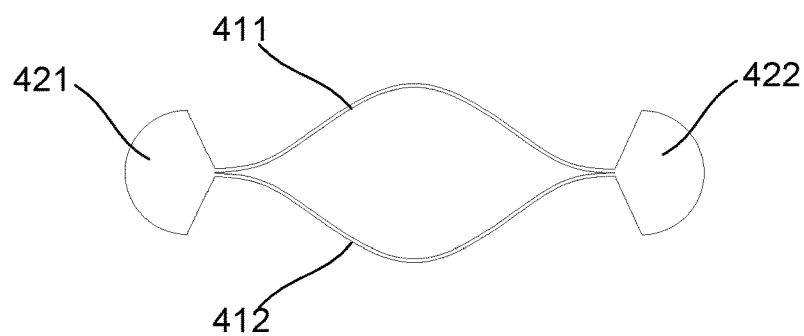
FIG. 4A is a schematic plan view of a third example of apparatus for closing a tissue opening.
Figure 4B:
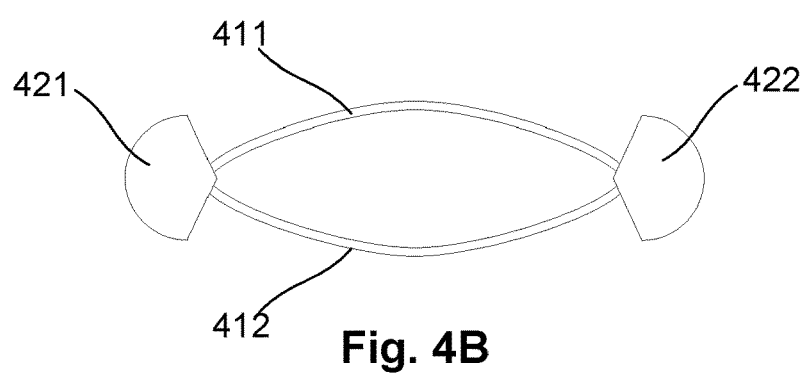
FIG. 4B is a schematic plan view of a fourth example of apparatus for closing a tissue opening.
Figure 4C:
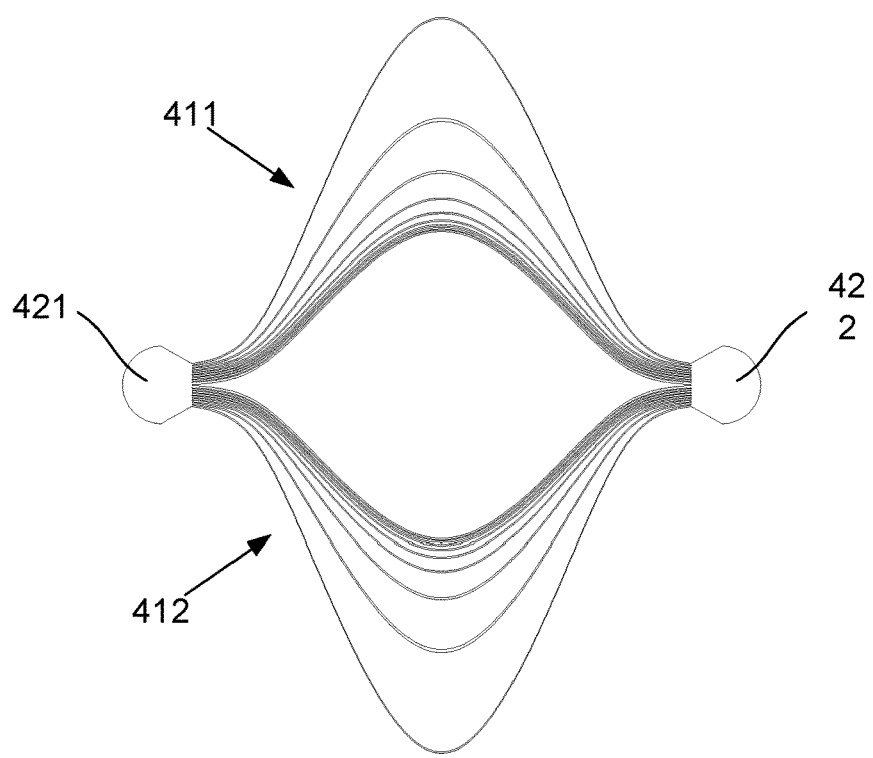
FIG. 4C is a schematic plan view of a fifth example of apparatus for closing a tissue opening.

Again first and second ends of the arms 311, 312 terminate or are coupled to respective arm end portions 321, 322, which in this example act as tabs to allow the user to manually bias the arms, as well as to adhere to the tissue surface to remain in a biased state. In this example, the arm end portions 321, 322 are substantially T-shaped, which can assist the user in holding the tabs, whilst also increasing the available surface area for adhering the tabs to the tissue surface T. It will be appreciated from this that the arm end portions could be of any suitable shapes and the examples shown are for the purpose of illustration only and are not intended to be limiting. In this regard, alternative configurations are shown in FIGS. 4A to 4C.

The use of multiple spaced first and second arms 311, 312 has a number of affects. For example, it increases the effective surface area of the arms compared to the example of FIGS. 1A to 1E, which in turn provides for greater coupling strength between the apparatus 300 and the tissue. This in conjunction with the larger end portions allows greater closing forces $F_C$ to be applied to the tissue opening, whilst also reducing the likelihood of the apparatus 300 being inadvertently removed. Accordingly, this allows the apparatus to be used with more extensive wounds.

Furthermore, in this example, the radius of curvature is greater for arms 311, 312 that are further away from the tissue opening O. Consequently, the first and second arms further away from the tissue opening O have a greater length, meaning that the mid-portions of the arms are spaced further apart moving away from the tissue opening O and that biasing of the first and second arms causes a progressively smaller degree of lateral movement further away from the tissue opening. Thus, for example, the mid-portion of the inner arm 311.1 moves a significantly greater distance that the mid-portion of the outer arm 311.2. As a result the degree of movement distributes tension through the tissue surface, with forces on the tissue being spread outwardly from the tissue opening, and gradually increasing towards the tissue opening. Thus, it will be appreciated that the arms are arranged so that mid-portions of the arms further away from the tissue opening have greater spacing and move a smaller distance, to thereby distribute tension within the tissue surface. This helps spread the tension in the tissue over a wider area, whilst ensuring that there is sufficient closing force along the tissue opening boundary to adequately close the tissue opening.

Accordingly, it will be appreciated that the use of multiple arms spaced outwardly from the tissue opening can improve the effectiveness of the arrangement, improving the durability and strength and allowing for greater control in the closing forces applied to the tissue opening and tension in the surrounding tissue.

Further examples of apparatus for closing a tissue opening are shown in FIGS. 4A to 4C. In these examples, similar features to those shown in FIGS. 3A to 3D are shown with reference numerals increased by 100, and these will not be described in detail.

In the example of FIG. 4A different shapes of arm end portions 421, 422 are shown, highlighting that any shape could be used, depending on the preferred implementation. In the example of FIG. 4B, a parabolic profile is used for the arms 411, 412. In this example, the parabolic shape is not as effective as the curves of the previous examples as it does not allow for the same degree of straightening, and hence typically results in reduced movement of the mid-portion of the arm, and hence less tissue closing force for a given biasing force. Nevertheless this can be useful in some applications.

In the example of FIG. 4C, an alternative profile is provided for the arms 411, 412, which includes a greater degree of curvature and hence spacing of the mid-portions, thereby allowing tension to be distributed over a greater tissue area.

Figure 5A:
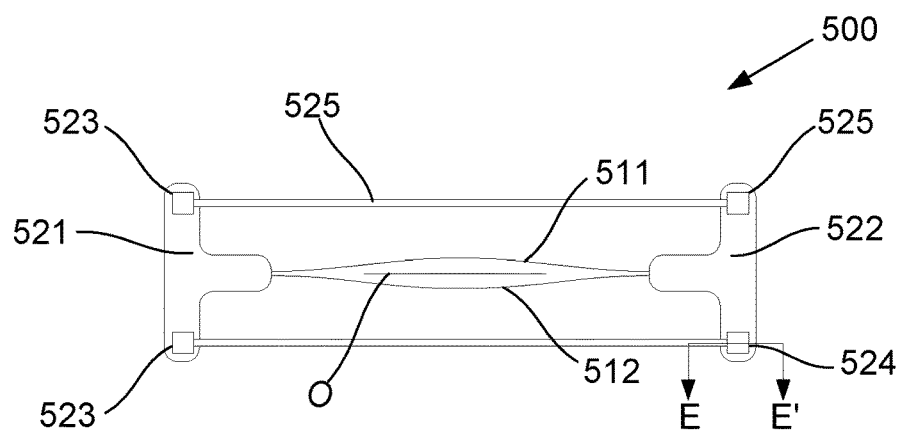
FIG. 5A is a schematic plan view of a sixth example of apparatus for closing a tissue opening.
Figure 5B:
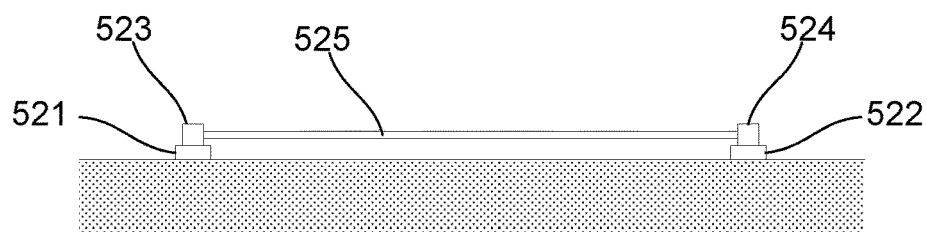
FIG. 5B is a schematic side view of the apparatus of FIG. 5A.
Figure 5C:
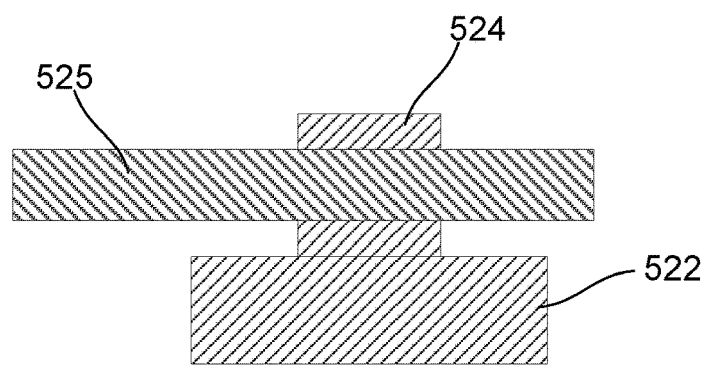
FIG. 5C is a schematic close-up cross sectional view along the line E-E' of FIG. 5A.

A sixth example of apparatus for closing a tissue opening will now be described with reference to FIGS. 5A to 5C. In this example, similar features to those shown in FIGS. 3A to 3D are shown with reference numerals increased by 200, and these will not be described in detail.

In this example, at least one biasing member 525, in this example in the form of two biasing arms, is provided extending between the arm end portions 521, 522. The biasing member(s) 525 may be coupled to the arm end portions 521, 522 using mountings, shown generally at 523, 524, although any suitable technique could be used. The biasing arms operate to bias the arm end portions 521, 522 apart, and this can be used to help reduce loading on the arm end portions 521, 522. In particular, if biasing is provided solely by adherence of the arm end portions 521, 522 to the tissue surface, the tension in the arms can results in the arm end portions decoupling from the tissue surface. However, the use of a biasing member allows the tension in the arms to be accommodated by the biasing member, thereby reducing the load on the arm end portions.

It will be appreciated that for this arrangement to function, the biasing members 525 must be capable of being placed under compression once the arm end portions have been biased apart. This can be achieved in any suitable manner, for example by providing biasing members that are telescopic and can be locked into position once extended. Alternatively, the biasing members 525 could be selectively or adjustably coupled to the arm end portions. For example, the biasing members 525 could be fixed to one of the arm end portions 521, and then only attached to the other arm end portion 522, once the arm end portions are correctly positioned. Alternatively the coupling could be adjustable, for example, by having the biasing member 525 slidably received in an aperture of the mounting 524, with the biasing member 525 being locked or held in position once the desired tension in the arms 511, 512 has been achieved. This could be achieved using teeth within the aperture that lock into corresponding teeth on the biasing member, a fastener extending through the mounting and biasing member, or a screw thread arrangement, similar to the arrangement described in more detail below with reference to FIGS. 7A to 7D.

A seventh example of apparatus for closing a tissue opening will now be described with reference to FIGS. 6A to 6D. In this example, the apparatus includes similar features to those shown in FIGS. 3A to 3D with reference numerals increased by 300, and these will not be described in detail.

In this example, the arm end portions 621, 622 are coupled to a frame 630. The frame 630 acts to anchor the arm end portions 621, 622 apart in the biased position, and therefore functions in a similar manner to the biasing member(s) described above. Thus, this can operate to accommodate tension in the arms 611, 612 by ensuring the biasing force is taken up by the frame 630 and not the tissue, thereby ensuring forces on the tissue are reduced. Additionally, the frame can optionally be coupled to the tissue to thereby assist in coupling the apparatus to the tissue around the tissue opening. In this example the frame 630 completely surrounds the arms 611, 612 and arm end portions 621, 622, however, this is not essential, and the frame 630 could extend around some or all of a perimeter of the apparatus.

The frame 630 can further act to provide additional structural rigidity and/or can be flexible allowing it to confirm to the shape of part of the subject. A combination of rigid and flexible sections may also be used depending on the preferred implementation.

In one example, once coupled to the tissue, the frame 630 defines a perimeter surrounding the tissue opening. In this configuration, the frame 630 can immobilise tissue within the perimeter so that the tension applied to the tissue is maintained at a constant level and is not altered by forces external to the frame 630. This means that as the subject moves, for example as part of day to day activities, the tissue opening is maintained in a constant state, without changes in the applied force. This has two main benefits. Firstly, this ensures that the correct closing/opening force is applied to the tissue opening and secondly promotes healing of the wound. For example, once an optimum closing force has been applied to the wound, and healing begins, the tissue remains undisturbed even during movement of the subject and surrounding tissue. This prevents rupturing or shearing of the healing tissue, which in turn allows healing to occur more rapidly. The combination of ideal closing force and immobilisation during healing lead to scarless healing of the wound.

The frame 630 can be of any suitable form and may be made of a biocompatible material or alternatively, a core with a biocompatible coating. The frame 630 could be made of a polymer such as high density polyethylene, polypropylene or the like, metal, such as stainless steel or the like or a combination thereof and can be manufactured using any suitable technique such as moulding, additive printing or the like.

The frame 630 can be coupled to the tissue surface by any suitable coupling mechanism such as an adhesive surface provided on an underside of the arm end portions or an adhesive layer provided on an underside of the arm end portions.

In the current example, the first arm end portion 621 is fixed to the frame 630, and optionally could be formed integrally with or as part of the frame 630. In contrast the second arm end portion 622 is movable relative to the frame 630 so that movement of the second arm end portion provides the biasing mechanism. In particular, the second arm end portion 622 is selectively secured to the frame 630 using a releasable fastener. This can be of any appropriate form, but in one example includes a plate 631 extending inwardly from the frame 630, which includes a releasable fastening mechanism that cooperates with the second arm end portion to secure the second arm portion thereto, for example, through the use of a hook and loop fastener, clips, buckles, or the like.

Figure 6A:
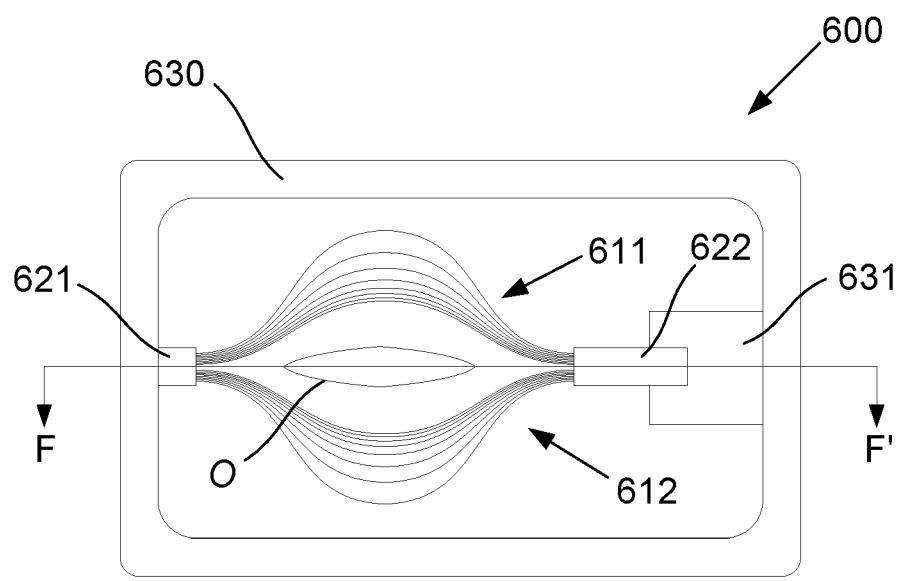
FIG. 6A is a schematic plan view of a seventh example of apparatus for closing a tissue opening with the apparatus in an open position.
Figure 6B:
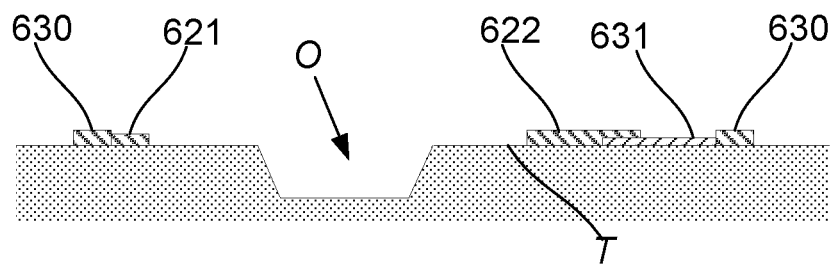
FIG. 6B is a schematic cross sectional view of the apparatus of FIG. 6A along the line F-F.
Figure 6C:
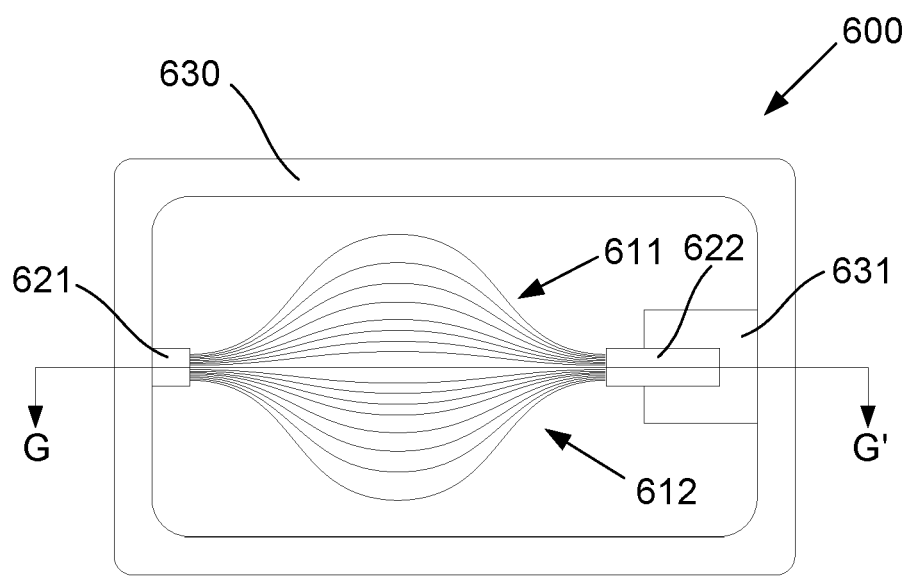
FIG. 6C is a schematic plan view of the apparatus of FIG. 6A in a closed position.
Figure 6D:
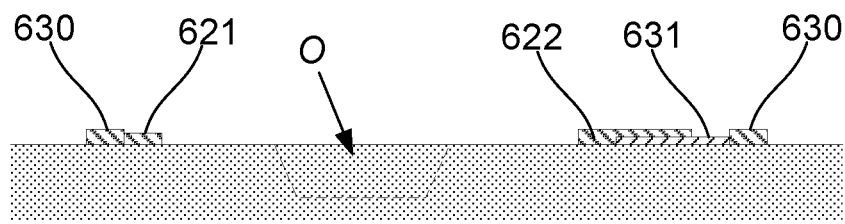
FIG. 6D is a schematic partial cross sectional view of the apparatus of FIG. 6C along the line G-G'.
Figure 7A:
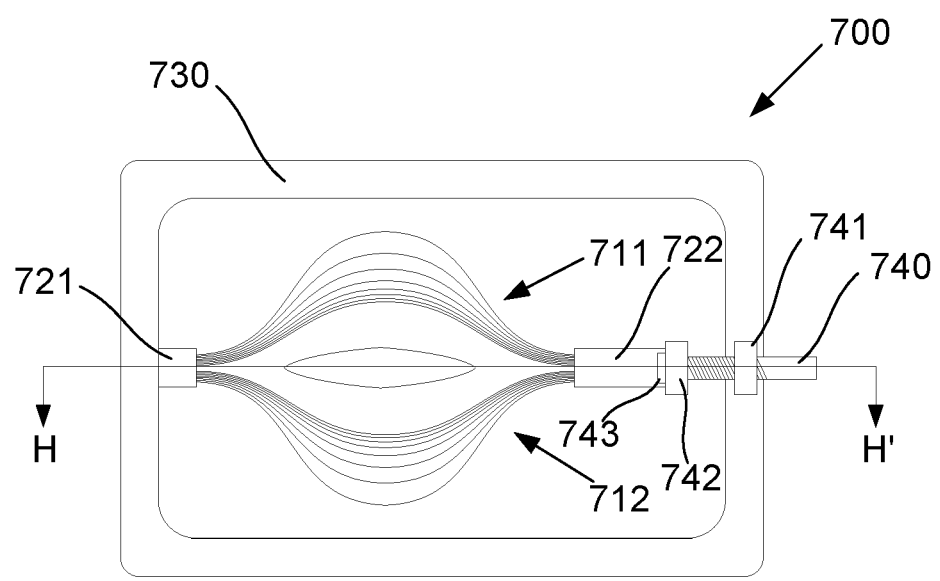
FIG. 7A is a schematic plan view of a eighth example of apparatus for closing a tissue opening with the apparatus in an open position.
Figure 7B:
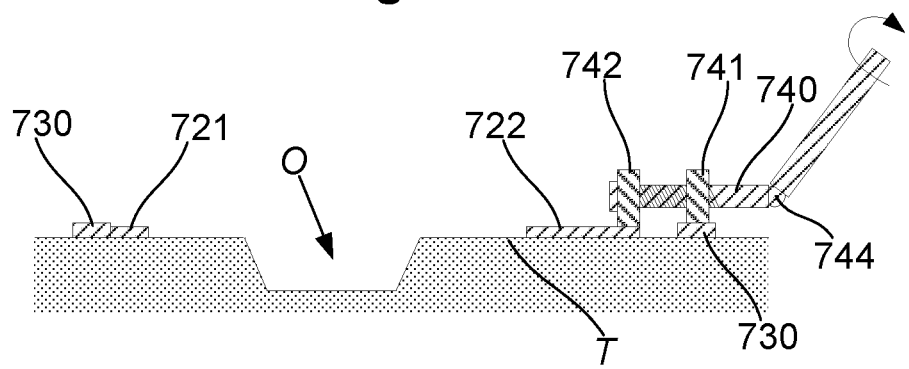
FIG. 7B is a schematic cross sectional view of the apparatus of FIG. 7A along the line H-H'.
Figure 7C:
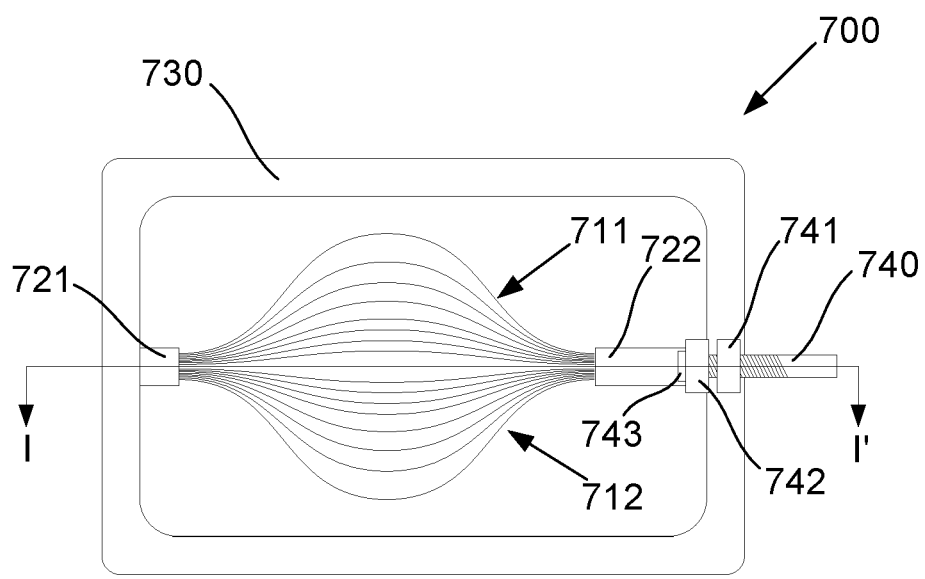
FIG. 7C is a schematic plan view of the apparatus of FIG. 7A in a closed position.
Figure 7D:
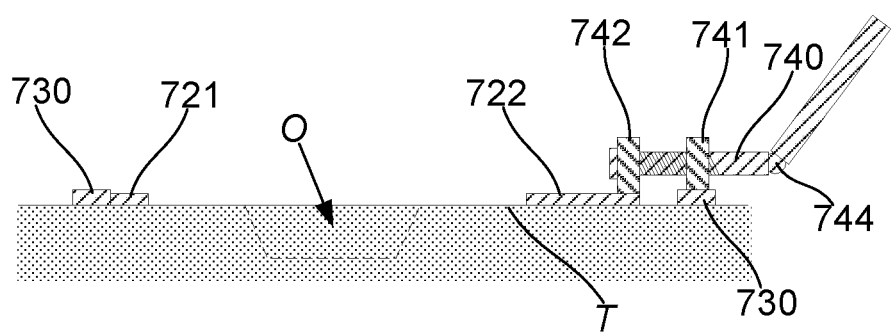
FIG. 7D is a schematic cross sectional view of the apparatus of FIG. 7C along the line I-I'.

In use, the arms 611, 612 and optionally the frame 630 would be coupled to the tissue T, as shown in FIGS. 6A and 6B. The second arm end portion 622 can then be decoupled from the plate 631, and urged away from the first arm end portion 621, thereby biasing the arms 611, 612 and closing the tissue opening. Once the tissue opening has been sufficiently closed, the second arm end portion is re-coupled to the plate 631, thereby retaining the arms 611, 612 in position.

Accordingly, it will be appreciated that in the above described example, the frame 630, and in particular the plate 631, acts to anchor the second arm end portion 622, thereby allowing this to be held in a desired position. By allowing the second arm end portion to be selectively recoupled to the plate 631, using a suitable fastening mechanism, this allows the biasing force $F_B$ applied to be adjusted, in turn allowing the closing force $F_C$ to be controlled. This can be done for a variety of reasons, such as for comfort, to reduce the closing force $F_C$ as the tissue opening heals, or to allow the force to be increased to accommodate additional loading, for example during exercise. It will be appreciated that this provides a mechanism for adjusting the closing force applied to the tissue opening, which in turn can maximise the effectiveness of the closing process, whilst minimising discomfort.

Thus, in the above example, the apparatus can be applied by applying a frame and arms to tissue surrounding a tissue opening and then adjusting a position of the arm end portion relative to the frame to thereby bias opposing ends of each arm apart and hence close the tissue opening.

A further example of apparatus for closing a tissue opening will now be described with reference to FIGS. 7A to 7D. In this example, the apparatus include similar features to those shown in FIGS. 6A to 6D and similar reference numerals are used albeit with reference numerals increased by 100, and these will not be described in detail.

In this example, an alternative biasing mechanism is provided which includes a threaded member 740, such as bolt, coupled to the second arm end portion 722 and the frame 730 so that rotation of the threaded member adjusts a separation of the second arm end portion 722 and the frame 730.

In the current example, first and second bolt mountings 741, 742 are provided on the frame 730 and the second arm end portion 722 respectively, with the bolt mountings 741, 742 including apertures for receiving the bolt 740 therein. The first bolt mounting 741 has a threaded aperture, so that rotation of the bolt 740 causes longitudinal movement of the bolt 740 within the first bolt mounting 741. The bolt includes a head 743 that abuts against the second bolt mounting 742, so that rotation of the bolt in a first direction can bias the arms 711, 712, thereby increasing the closing force applied $F_C$ to the tissue opening. Conversely, rotation of the bolt in a second opposing other direction will unbias the arms 711, 712 so that resilience of the arms 711, 712 returns them towards their original position, thereby reducing the closing force applied $F_C$ to the tissue opening. The bolt 740 may include a flexible section, flexible torque transmission system, universal joint 744, or the like, to facilitate access to the bolt 740 to allow it to be easily rotated.

Accordingly, in the above example, the use of the threaded arrangement allows the relative separation of the second arm end portion 722 and the frame 730 to be adjusted with a high degree of accuracy, thereby providing a significant degree of control over the closing force applied to the tissue opening, and allowing this to be easily adjusted without interfering with the tissue opening.

Further examples of apparatus including a frame will now be described with reference to FIGS. 8A and 8B. In this example, the apparatus 800 includes similar features to those shown in FIGS. 7A to 7D and similar reference numerals are used albeit with reference numerals increased by 100.

In these examples alternative designs of frame 830 are shown. The frame includes a greater surface area, allowing greater tension to be accommodated and optionally providing a greater surface area for coupling the frame to the tissue surface. It will be appreciated that in these examples no mechanism is shown for coupling the second arm portion 822 to the frame 830, but mechanisms similar to those described above can be used.

Figure 8A:
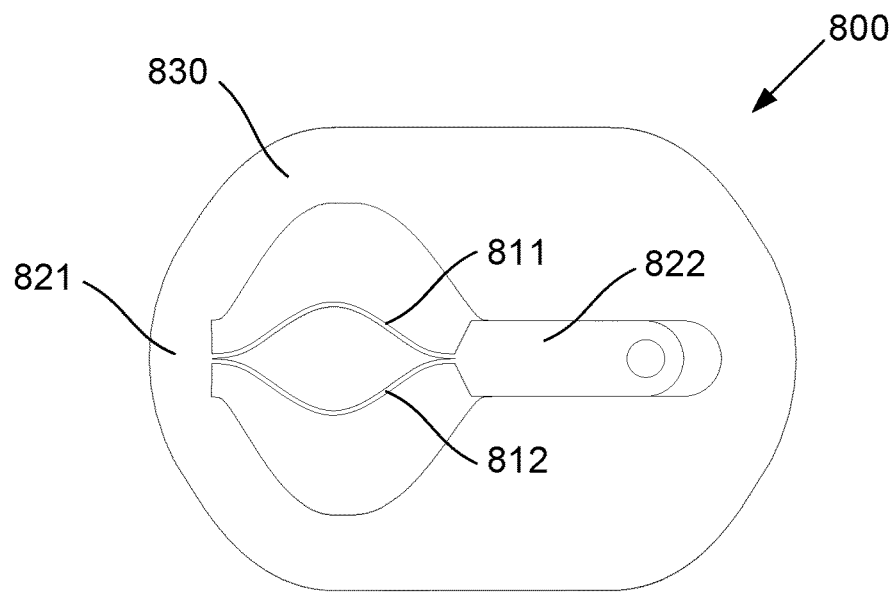
FIG. 8A is a schematic plan view of a ninth example of apparatus for closing a tissue opening.
Figure 8B:
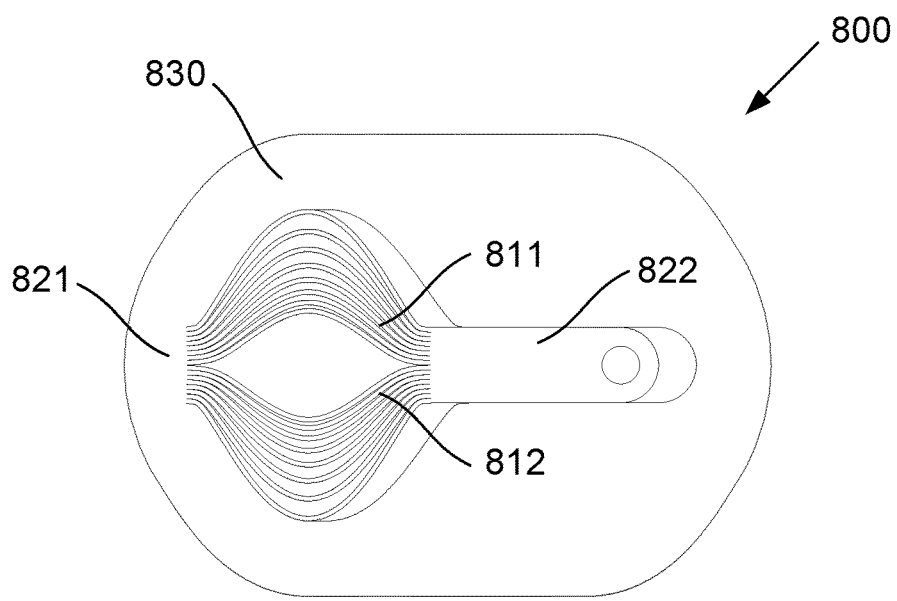
FIG. 8B is a schematic plan view of a tenth example of apparatus for closing a tissue opening.

In one example, the arrangements of FIGS. 8A and 8B can be formed from laser cutting of a sheet of material, such as stainless steel or the like, although any suitable arrangement could be used.

Further details of the arms will now be described with reference to FIGS. 9A and 9B and 10A and 10B.

Figure 9A:
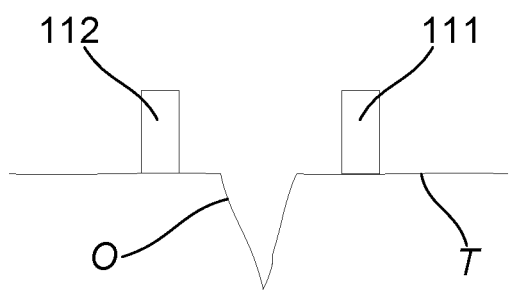
FIG. 9A is a schematic cross sectional view of first example of arms of an apparatus for closing a tissue opening with the apparatus in an open position.
Figure 9B:
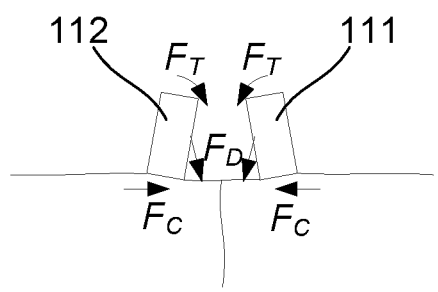
FIG. 9B is a schematic cross sectional view of the arms of FIG. 9A with the apparatus in a closed position.

In this example of FIGS. 9A and 9B, arms 111, 112 having a substantially upstanding rectangular cross section are shown. In this example, biasing of the arms generates a torsional force $F_T$ in the mid-portions of the arms 111, 112, which in turn results in a downward force $F_D$ on the tissue surface, particularly on either side of the tissue opening between the arms, as shown by depression of the tissue surface between the arms 111, 112. Such a downward force can assist with closing and sealing of the tissue opening, as well as reducing scaring. Whilst the creation of torsional forces can be achieved with other cross sectional shapes, the rectangular shape is particularly beneficial as this maximises the effect, thereby minimising scarring as much as possible.

Figure 10A:
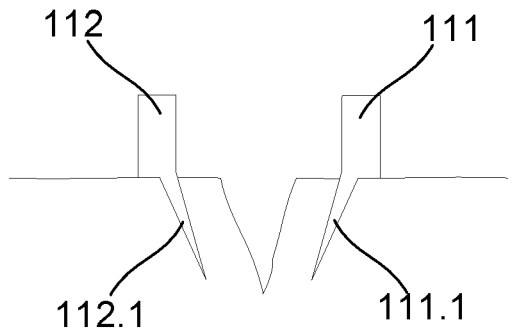
FIG. 10A is a schematic cross sectional view of second example of arms of an apparatus for closing a tissue opening with the apparatus in an open position.
Figure 10B:
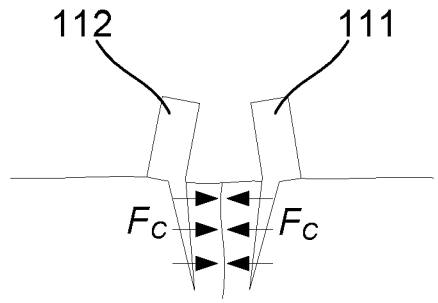
FIG. 10B is a schematic cross sectional view of the arms of FIG. 10A with the apparatus in a closed position.

In the example of FIGS. 10A and 10B the arms 111, 112 include projections 111.1, 112.1, such as micro-needles or teeth, that extend from an underside of the arms 111, 112 and penetrate the tissue surface in use. The projections 111.1, 112.1 can assist in coupling the arms 111, 112 to the tissue and can be used instead of or in addition to adhesive material. The projections can be of any length depending on the desired implementation, and in particular the desired penetration into the subject.

In this regard, the projections can assist in generating a closing force in the dermal layers below the tissue surface thereby closing the tissue opening below the tissue surface, as shown in FIG. 10B. In this instance, the length of the projections could be selected based on a desired penetration depth, so for example if it is desired to penetrate the dermis, but not subcutaneous tissue, the projections would typically by about 500 nm or less in length.

Additionally, the projections can be adapted to deliver a bioactive material into the tissue around the tissue opening, for example by coating the projections in a suitable material. This can be used to deliver healing agents, such as anti-inflammatory agents to reduce post-operative or post trauma swelling, anti-bacterial, viral or microbial agents or the like to reduce the likelihood of infection, anti-coagulants, anti-scarring agents, or the like.

Figure 11:
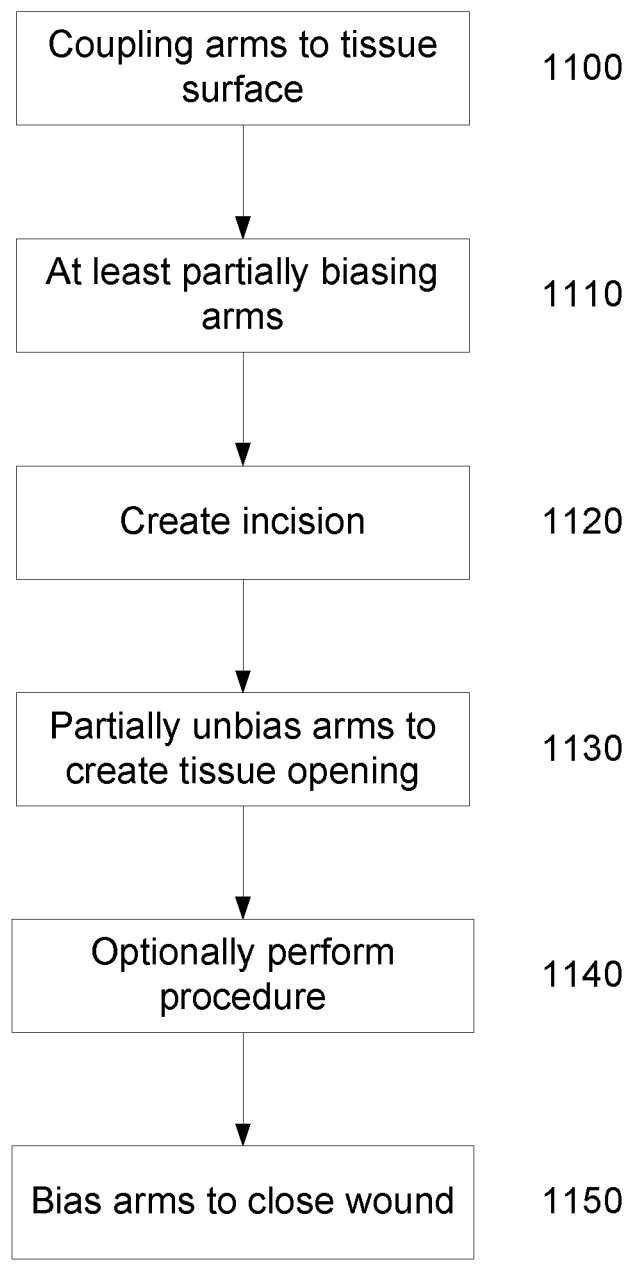
FIG. 11 is a flow chart of an example of a method of opening and closing a tissue opening.

Accordingly, the above describes methods and apparatus for closing a tissue opening such as a wound. However, use of the apparatus is not so limited, and in a further example, the apparatus can be used to assist in creating a tissue opening, for example as part of a surgical procedure, as will now be described with reference to FIG. 11.

In this example, at step 1100 the method includes coupling at least two flexible arms to the tissue, wherein in an unbiased state the arms are resilient and naturally curved in at least a mid-portion. At step 1110 opposing ends of the arms at least partially biased apart so that the arms are at least partially straightened, before an incision is created in the tissue between the arms at step 1120. This process would typically be performed by a surgeon or the like using suitable equipment such as a scalpel. At this point, as the arms are partially biased, even though the tissue is cut, it is generally held together by the closing force generated by the arms.

At step 1130, the arms are at least partially unbiased so that resilience of the arms causes the mid-portions to move apart to thereby open the incision and create a tissue opening. A surgical procedure can now be performed at step 1140, before the opposing ends of each arm are biased apart to thereby at least partially straighten the arms, which in turn biases the mid-portions towards each other to at least partially close the tissue opening. In this regard, it will be appreciated that the arms are typically biased using a greater biasing force in step 1150 than in step 1110, thereby ensuring that the tissue opening fully closes with a resulting closing force being applied to the tissue to hold the tissue closed.

Accordingly, it will be appreciated that this provides a mechanism for creating and then reclosing a tissue opening. This has a number of benefits. For example, this allows the opening to be created in a controlled manner and then subsequently reclosed rapidly, minimising stress on the subject. Additionally, during the creation of the opening, tension within the tissue is taken up by the apparatus, reducing the likelihood of unwanted tissue tearing and scarring. For example, during keyhole surgery or the like, implements will be inserted into the opening, which can strain the opening. However, using the above described apparatus, the additional forces can be taken up by the apparatus and distributed more widely through tissue around the opening and not just through tissue in the opening wall, thereby helping minimise damage.

A number of further variations can also be performed. For example, the tissue can be opened progressively. In this regard, an initial incision can be created and opened by partially, with a further incision being created within the tissue opening, allowing the opening to open further. It will be appreciated that this allows the extent of the opening to be gradually increased so that the minimum possible size of opening is created.

Additionally, once the opening is closed, it is typical to re-examine the opening on a periodic basis to ensure this is closing. This can be achieved by gradually relaxing the arms, so that they return to the unbiased state and monitoring the tissue opening during this process. In this regard, it will be appreciated that this is facilitated by the unobstructed access to the opening provided by the arms being provided on either side of the opening. The apparatus can also be removed and replaced as required.

Whilst any of the above described apparatus arrangements could be used when creating an opening, it will be appreciated that apparatus described in the example of FIGS. 7A to 7D is particularly beneficial as this can provide a high degree of control over the tissue opening process.

A further example of an apparatus for closing and opening a wound will now be described with reference to FIGS. 12A to 12H.

In this example, the apparatus 1200 includes arms 1211, 1212 coupled to a frame 1230 so that a biasing mechanism can be used to at least partially deform the frame 1230 to thereby bias opposing ends of each arm 1211, 1212 apart, which in turn causes mid-portions of the arms to close. Thus, in contrast to above arrangements the apparatus 1200 can use a deformable frame 1230 in order to control opening and/or closing of arms 1211, 1212 and hence opening and/or closing of tissue openings.

In one particular example, the biasing mechanism includes a drive ring 1240 that engages the frame 1230, with the frame 1230 and drive ring 1240 being configured so that the frame 1230 deforms upon relative rotation of the frame 1230 and drive ring 1240.

This can be achieved using an appropriately shaped frame 1230 and drive ring 1240, for example by having these made of complimentary elliptical shapes. In this example, when the drive ring 1240 is coupled to the frame 1230 and rotated as shown in FIGS. 12C to 12F, the frame 1230 is gradually deformed, thereby urging ends of the arms 1211, 1212 apart and progressively reducing the separation of mid-portions of the arms. It will be appreciated that this in this example, this allows a degree of rotation of the drive ring 1240 to be used to adjust biasing of the arms 1211, 1212, and hence a closing or opening force applied to tissue around a tissue opening.

Whilst the current example uses an elliptical frame 1230 and drive ring 1240 combination, it will be appreciated that other configurations could be used depending on the preferred implementation.

In this example, the apparatus 1200 includes sets of first and second arms 1211, 1212 positioned on either side of the tissue opening, with the arms 1211, 1212 being coupled to respective arm end portions 1221, 1222. The arm end portions 1221, 1222 are in turn coupled to the frame 1230, so that deformation of the frame causes movement of the arm end portions 1221, 1222 and hence the ends of the arms 1211, 1212.

In this example, each set of arms 1211, 1212 includes three arms, but it will be appreciated that this is for the purpose of illustration only and is not intended to be limiting. In practice a greater number of arms would typically be used, with the number typically depending on factors such as manufacturing techniques and materials, the degree of force required to be exerted on the tissue opening or the like.

In the current example, the frame 1230 is substantially elliptical, whilst the innermost arms 1211.1, 1212.1 are substantially circular, with the intermediate arms 1211, 1212 being progressively shaped from circular towards elliptical moving outwardly from the inner most arms 1211.1, 1212.1. This helps provide decreasing amounts of movement of the mid-portions of the arms 1211, 1212 moving outward from the innermost arms 1211.1, 1212.1, thereby distributing forces across the tissue surface.

The frame 1230 typically includes a lip 1231 projecting upwardly from and extending around at least part of a perimeter of the frame 1230. In use, the drive ring 1240 engages the lip 1231, thereby deforming the frame 1230. The drive ring 1240 is generally shaped to conform to the shape of the frame 1230, and in particular the lip 1231, so that the drive ring 1240 engages the entire length of the lip 1231. This can be used to maximise engagement between the frame 1230 and drive ring 1240, allowing the drive ring to be retained in position using frictional engagement with the lip 1231. However, this is not essential and other arrangements could be used, such as coupling the frame 1230 and drive ring 1240 using clip fit, interference fit, and/or other similar arrangements.

The frame 1230 is typically elastically deformable so that it naturally returns to a rest position. Accordingly, the frame 1230 and arms 1211, 1212 are typically made of a resilient biocompatible material, such as plastic, acrylic, or the like, although other suitable materials could be used. The frame 1230 and arms 1211, 1212 can be manufactured using any suitable technique, such as molding, injection molding, laser cutting, additive printing or the like, depending on the preferred implementation and desired material characteristics. The drive ring 1240 is typically formed from a non-deformable material such as steel, a high density plastic, or the like. This allows the drive ring 1240 to accommodate forces generated through elastic deformation of the frame 1230, whilst providing structural rigidity, allowing the arms 1211, 121 and frame 1230 to conform to the shape of the subject's body. For example, this allows the apparatus to flex relative to the plane of the apparatus, so that it can be positioned on curved surfaces, whilst still providing sufficient radial rigidity within the plane of the apparatus, to thereby apply the required opening/closing forces to the incision or wound.

The drive ring and/or frame could have polished surfaces or be provided with low friction coatings, to reduce friction between the drive ring and frame, allowing for easy rotation of the drive ring relative to the frame, which in turn reduces torsional forces on the body and subject when the drive ring is being rotated.

Figure 12A:
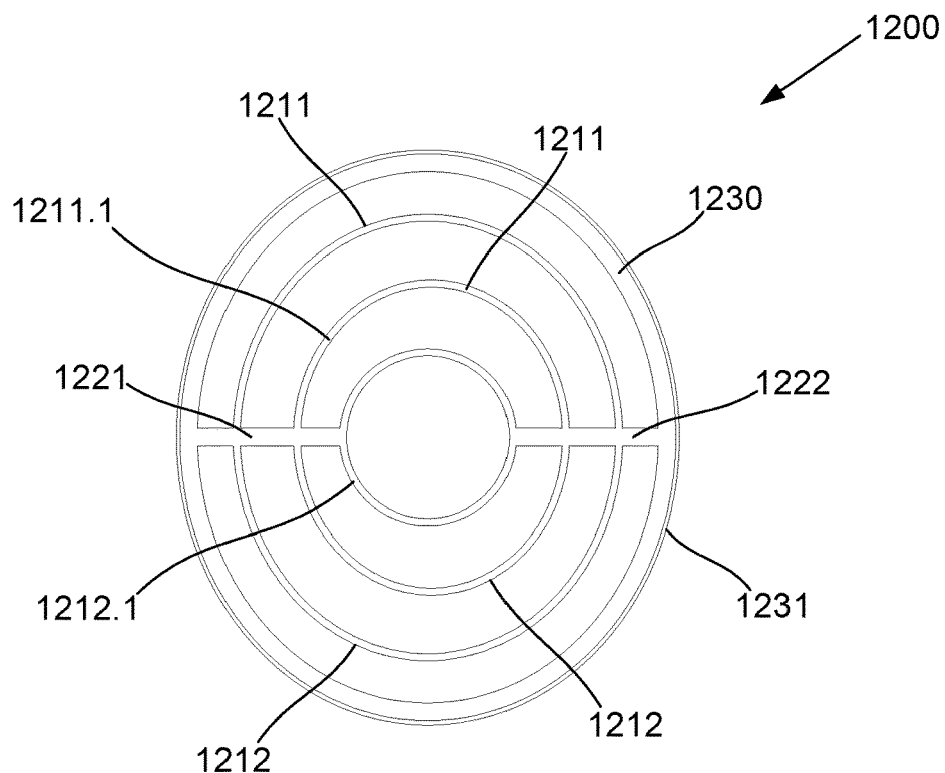
FIG. 12A is a schematic plan view of a further example of apparatus for closing a tissue opening with the apparatus in the open position.
Figure 12B:
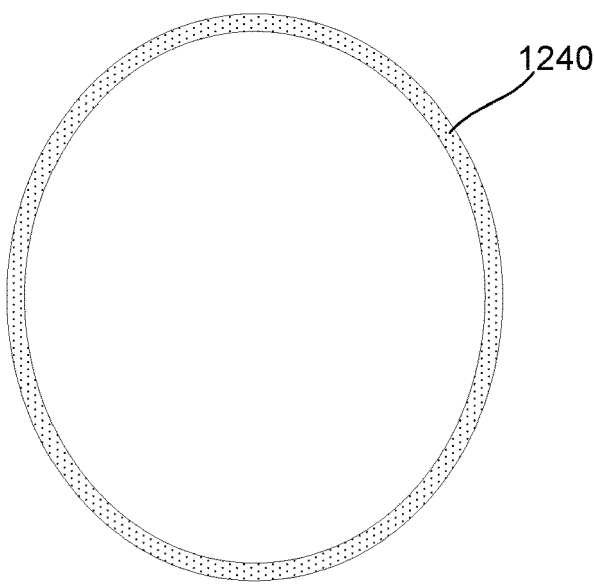
FIG. 12B is a schematic plan view of an example of a drive ring.
Figure 12C:
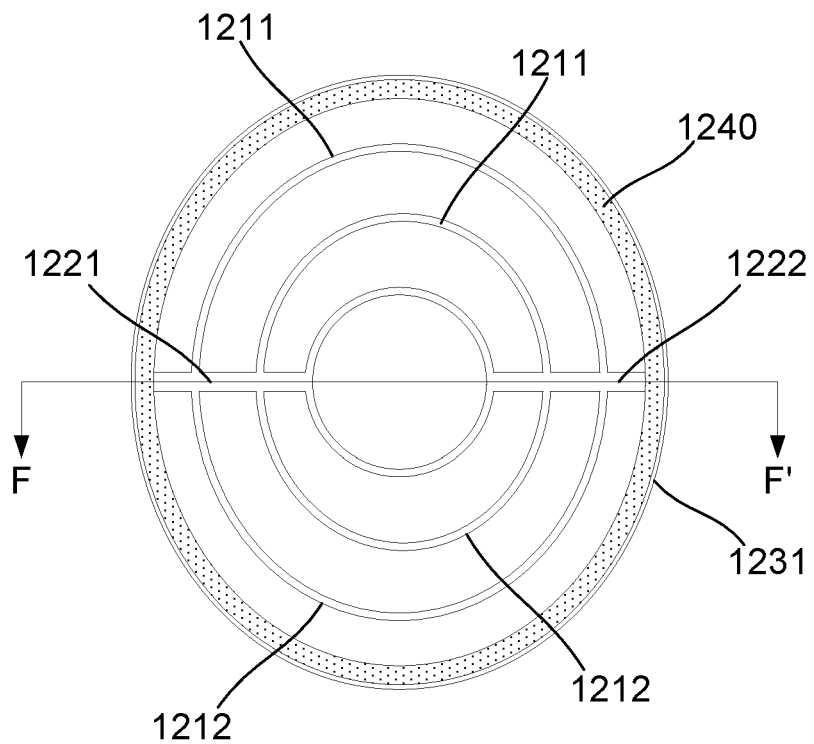
FIG. 12C is a schematic plan view of the apparatus of FIG. 12A with the drive ring of FIG. 12B coupled thereto.
Figure 12D:
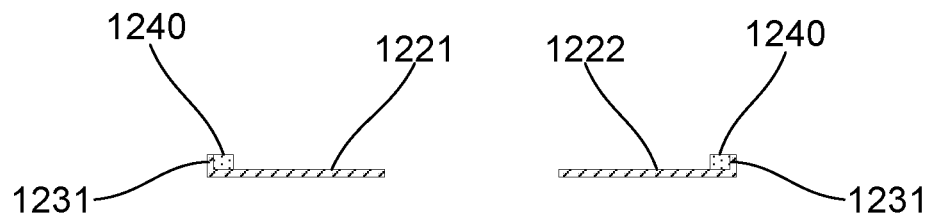
FIG. 12D is a schematic cross sectional view along the line F-F' of FIG. 12C.
Figure 12E:
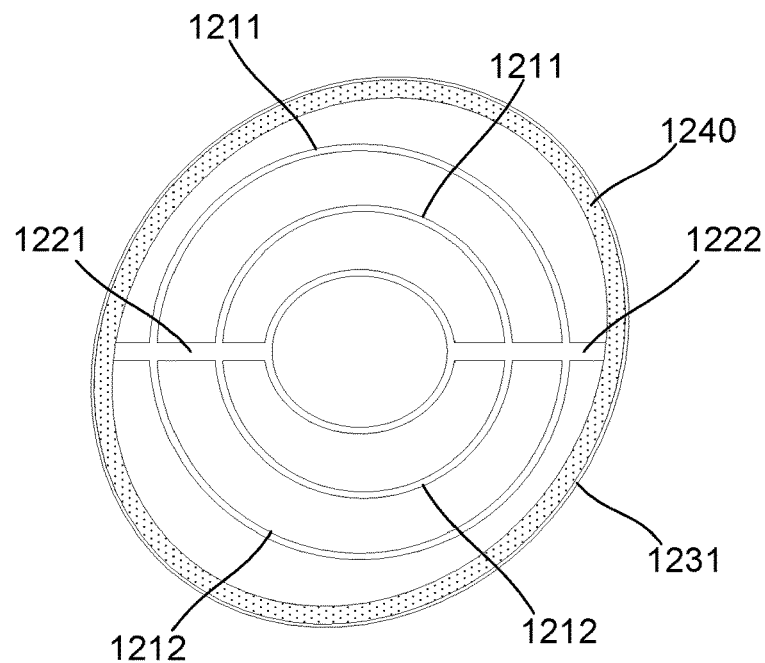
FIG. 12E is a schematic plan view of the apparatus of the FIG. 12A in a partially closed position.
Figure 12F:
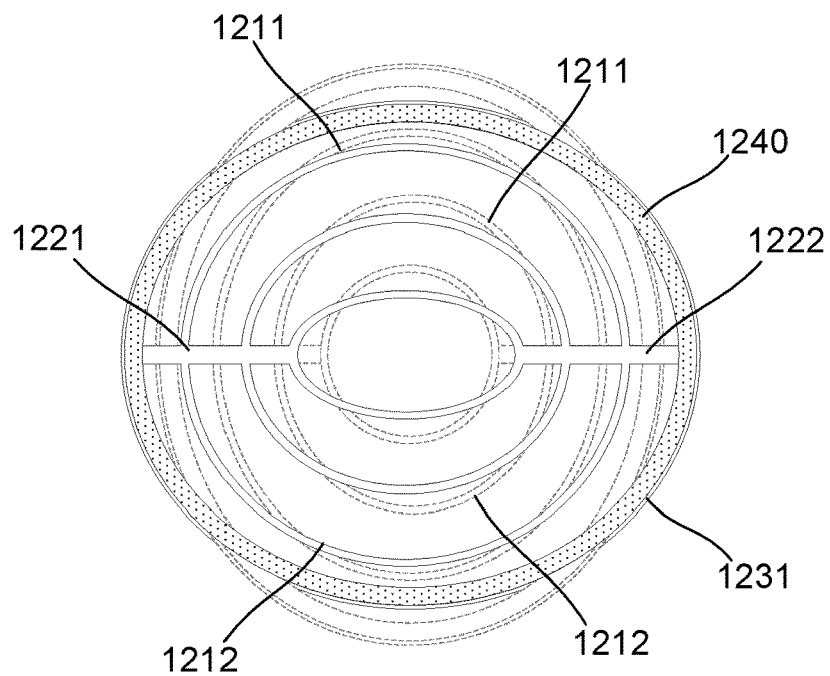
FIG. 12F is a schematic plan view of the apparatus of FIG. 12A in a fully closed position.

In the current example, the frame 1230 and arms 1211, 1212 are configured so that the unbiased rest position is as shown in FIG. 12A, with the arms 1211, 1212 extending between arm end portions 1221, 1222 at the narrowest part of the frame 1230. In this case, action of the drive ring 1240 operates to urge arm ends apart, thereby reducing the separation between the arm mid-portions to thereby close a tissue opening. However this is not essential and alternatively the frame 1230 could be naturally biased into the closed position shown in FIG. 12F so that action of the drive ring 1240 is required to open the arms.

The above described arrangement has a number of advantages. In particular, cooperation of the frame 1230 and drive ring 1240 allows progressive closing or opening of the first and second arms 1211, 1212, which provides a high degree of control over the pressure applied to the tissue opening, either when opening and/or closing the opening. This can help ensure adequate closing forces are applied to the opening to allow healing, whilst preventing undue forces being applied, which helps reduce scarring, as well as allowing the applied forces to be reduced over time as the opening heals. This also allows incisions to be opened progressively, for example during surgery or the like, thereby minimising tissue damage, whilst allowing a sufficiently large opening to be created for surgical purposes.

Secondly, the arrangement is self-supporting, with the drive ring 1240 providing additional stiffness to the frame 1230 ensuing that frame 1230 remains deformed at the desired amount even under the application of external forces. In particular, this leads to immobilisation of the tissue within the perimeter of the frame 1230 and drive ring 1240, so that forces applied to tissue surrounding the device, for example through movement of the subject, do not result in corresponding forces within the perimeter. Accordingly, once a desired opening/closing force has been applied to the tissue opening, this is maintained until the position of the drive ring 1240, and hence the shape of the frame 1230, is adjusted. As previously described, in terms of wound closing, this helps promote scarless healing, whilst in the case of opening a surgical incision, this minimises disruption to the tissue during surgery, reducing bruising and other injury during the procedure. Thus, it will be appreciated that the either or both of the frame and drive ring can at least partially immobilise tissue within a perimeter of the frame, which in turn can promote healing or reduce the impact of surgery.

This also enables the arms and frame to more closely conform to the body shape of the subject, maximising the effectiveness of bonding of the device to the subject.

Thirdly, as the frame 1230 is typically adhered to the subject, deformation of the frame 1230 will deform the subject's tissue both inside and outside of the frame perimeter, meaning forces are more widely distributed across the tissue, allowing a sufficiently large force to be applied to the tissue opening, whilst dispersing the resulting compression/tension in the tissue over as wide a surface area as possible.

Figure 12G:
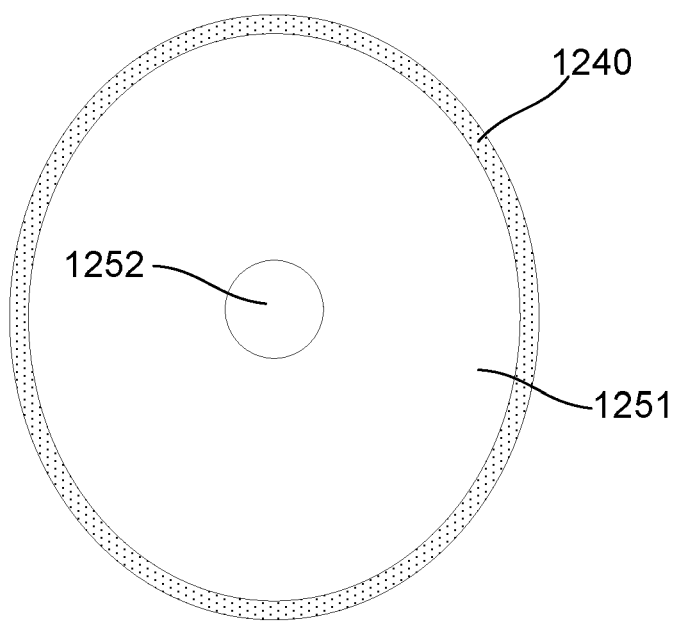
FIG. 12G is a schematic plan view of an actuator for use with the arrangement of FIG. 12C.
Figure 12H:
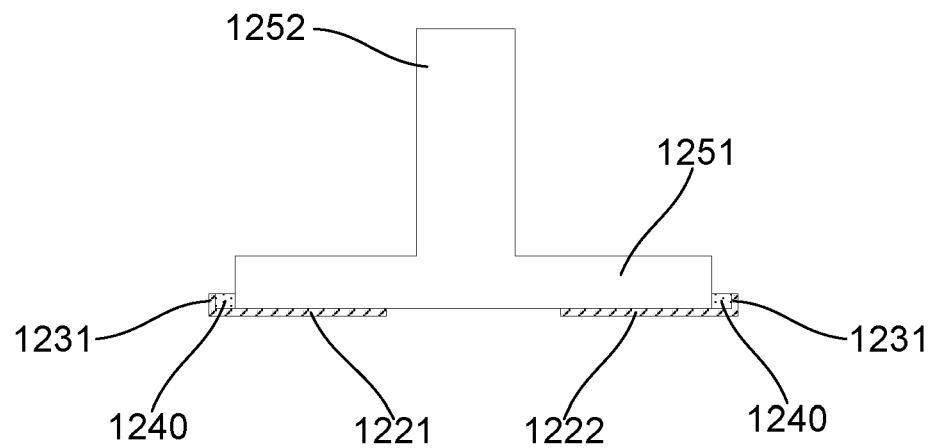
FIG. 12H is a schematic cross sectional view on the line F-F' with the actuator in place.

Thirdly, the drive ring 1240 can act as an interface to allow for the attachment of surgical tools during surgical procedures. By way of an example, to assist with adjustment of the drive ring 1240, an actuator 1250 can be provided which includes a body defining a key 1251 coupled to a handle 1252, as shown in FIGS. 12G and 12H. In use, the key 1251 engages the drive ring so that the drive ring 1240 can be rotated through rotation of the handle 1252. This makes it easy to operate the drive ring 1240, in particular allowing single handed adjustment of the apparatus to be performed.

In this example, the key 1251 is a complimentary shape to the drive ring 1240, and in particular is elliptically shaped so that the key 1251 engages an inner edge of the drive ring 1240. However, other engagement mechanisms could be used to couple the actuator 1250 to the drive ring, such as through the use of clip fit, interference fit, friction fit arrangements or the like.

It will also be appreciated however, that other tools, such as an optical system for viewing the tissue opening, a blade for creating an incision and a guide for guiding a surgical instrument or the like, could be connected in similar manners by having these engage the drive ring 1240 as will be described in more detail below.

A specific example of the apparatus of FIG. 12A to 12F for use in trocar surgery will now be described with reference to FIGS. 13A to 13E. In this example reference numerals are increased by 100 to identify similar features and these will not therefore be described in detail.

In this example, the apparatus 1300 includes two parts, namely the plastic body 1310, including the frame 1330 and arms 1311, 1312 and the drive ring 1340. The drive ring 1340 is located within tabs or slots inside the frame 1330, so that when the drive ring 1340 is rotated relative to the frame 1330, the frame 1330 and hence arms 1311, 1312 distort to thereby open or close a tissue opening, in a manner similar to that described above with reference to FIGS. 12A to 12H.

The drive ring 1340 is typically a simple SS316 stainless steel ring, 0.4 mm thick, formed into an ellipse approximately 47×39 mm, 2 mm wide. The body 1310 is typically made from 2 mm Acetal, with the frame 1330 and arms being 1 mm thick and including a 2 mm high lip 1331 around the edge of the frame 1330. The plastic element can be laser cut or CNC machined, printed or the like. These dimensions are suitable to accommodate a 5 mm trocar device, and it will be understood that these are for the purpose of illustration only and that other sizes could be used for other surgical devices or procedures.

The inner arms 1311.1, 1312.1 form a trocar ring for accommodating a trocar device as will be described in more detail below. Arm end portions 1321, 1322 connect the trocar ring arms 1311.1, 1312.1 to the frame 1330, so that when the drive ring 1340 is rotated a tensile force is exerted on the arm end portions 1321, 1322 which puts a tensile force onto the trocar ring arms 1311.1, 1312.1. This ring is centrally located and takes the form of a nominally circular ring when in an 'open' undistorted position. When the drive ring 1340 is rotated approx 80-85° within the device, the trocar ring distorts into a slot with parallel sides approx 3 mm apart.

Additional intermediate arms 1311, 1312 are also attached to the arm end portions 1321, 1322 between the trocar ring arms 1311.1, 1312.1 and the frame 1330 to define several concentrically mounted rings. These rings progressively move from a circular shape near the trocar ring, to a more elliptical shape near the frame 1330. As the device opens the intermediate arms 1311, 1312 move progressively together, conforming to the altered shape of the device. The intermediate arms 1311, 1312 provide additional bonding area and progressively spread the loads imposed by the device across the subject's tissue surface.

In this example, the trocar ring arms 1311.1, 1312.1 are coupled to the arm end portions 1321, 1322 via live hinges, which are curved portions shown in FIG. 13E that control the precise distortion of the trocar ring arms 1311.1, 1312.1 into a slot as the device moves from the 'open' position to the 'closed' position and back. Live hinges can also be used for the intermediate arms 1311, 1312.

In use, the drive ring 1340 is typically mounted to the frame 1330 and rotated to a desired position before the device 1300 is attached to the tissue of the subject using a suitable bonding agent, such as an adhesive, or the like.

An example of a surgical procedure utilising the above described arrangement will now be described with reference to FIGS. 14A to 14F. Whilst the following example is described with reference to the apparatus of FIGS. 12A to 12H it will be appreciated that this could equally apply to the apparatus of FIGS. 13A to 13E.

Figure 14A:
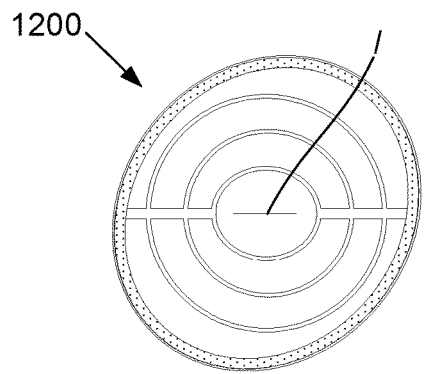
FIG. 14A is a schematic plan view of the apparatus of FIG. 12C when making an incision.

In this example, as shown in FIG. 14A the apparatus 1200 is initially biased towards an at least partially closed position using the drive ring 1240, with the apparatus 1200 then being attached to the subject and an incision I created between the arms 1211.1, 1212.1.

Figure 14B:
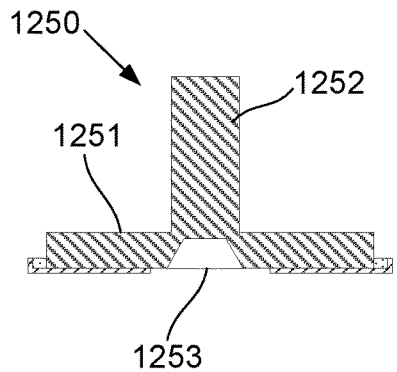
FIG. 14B is a schematic cross sectional view showing an actuator including an optical instrument.

The actuator 1250 is then coupled to the drive ring 1240 as shown in FIG. 14B. In this example, the actuator includes an imaging device 1253, such as a microscope and camera arrangement, allowing an image of the incision I and subsequent opening O to be captured and displayed on a monitor or other similar arrangement. This allows the surgeon or other operator to view the opening O as it is created even whilst the actuator 1250 is in place.

Figure 14C:
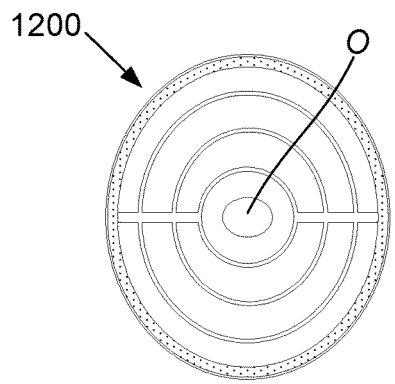
FIG. 14C is a schematic plan view of the apparatus of FIG. 12C when creating an opening.

The actuator 1250 and hence drive ring 1240 are then gradually rotated to an at least partially open position shown in FIG. 14C, so that the trocar arms 1211.1, 1212.1 and intermediate arms 1211, 1212 pull the incision I and surrounding tissue apart in a controlled manner to thereby form an opening O. It will be appreciated that the apparatus 1200 does not need to be fully opened, but rather need only be opened a sufficient amount to create an adequate sized opening, with the surgeon assessing when this has occurred using the imaging device 1253.

Figure 14D:
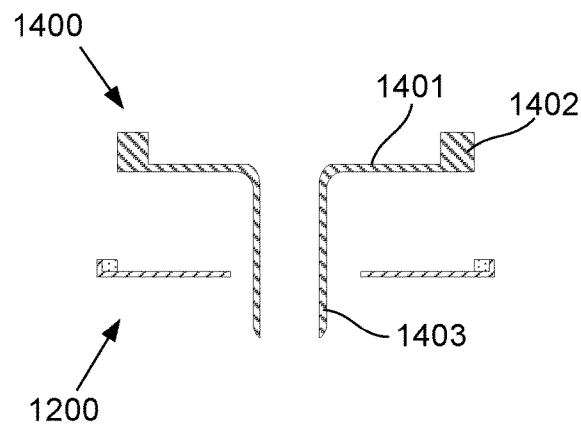
FIG. 14D is a schematic cross sectional view of the apparatus of FIG. 12C along the line F-F', with a trocar guide being inserted therein.
Figure 14E:
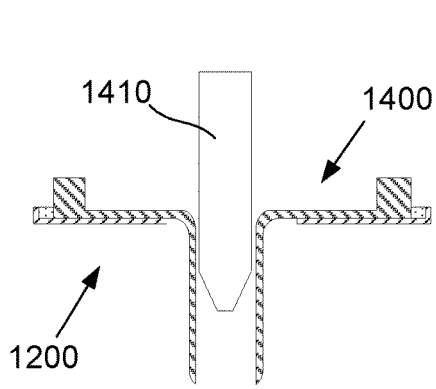
FIG. 14E is a schematic cross sectional view showing an insertion of a trocar surgical tool.
Figure 14F:
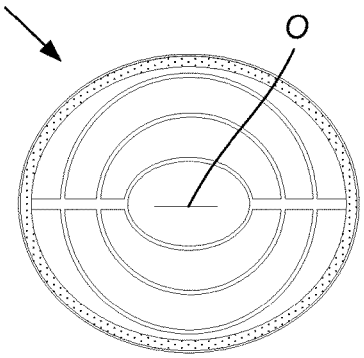
FIG. 14F is a schematic plan view of the apparatus of FIG. 12C used to close the wound opening.

Following the creation of the opening, the actuator 1250 is removed and a guide 1400 is coupled to the apparatus 1200 to guide insertion of a trocar device. In this regard, as shown in FIG. 14D, the guide 1400 includes a guide body 1401 having a lip 1402 that engages the drive ring 1240, thereby retaining the guide in position. Again this can be achieved using a friction fit, interference fit, clip fit or the like. The guide further includes a guide channel 1403 extending downwardly from the body 1401 so that the guide channel 1403 extends between the trocar ring arms 1211.1, 1212.1 and into the opening O.

Once the guide 1400 is in position, a trocar device 1410 can be inserted into the channel 1403 allowing this to be used to perform surgery. It will be appreciated by coupling the trocar guide 1400 to the drive ring 1240 and hence the apparatus 1200, this holds the guide 1400 in place so that it does not move within the subject, even upon application of forces by a surgeon. This vastly improves surgical outcomes and in particular reduces trauma and bruising to peripheral tissue surrounding the opening O.

Following completion of the surgical procedure, the trocar device 1410 and guide 1400 are removed from the tissue opening O, and the actuator 1250 replaced allowing this to be used to progressively close the apparatus 1200 and hence the tissue opening O. This can again be performed using a displayed image so that a surgeon can monitor the degree of closing and then fix the apparatus 1200 in position once a desired degree of closing is achieved.

Thus, it will be appreciated that the above described arrangement can be used to provide a high degree of precision and control over opening and closing of tissue openings, whilst also allowing for support of additional surgical tools, thereby making the system ideal for use in surgical procedures, such as keyhole surgery or the like.

Figure 15A:
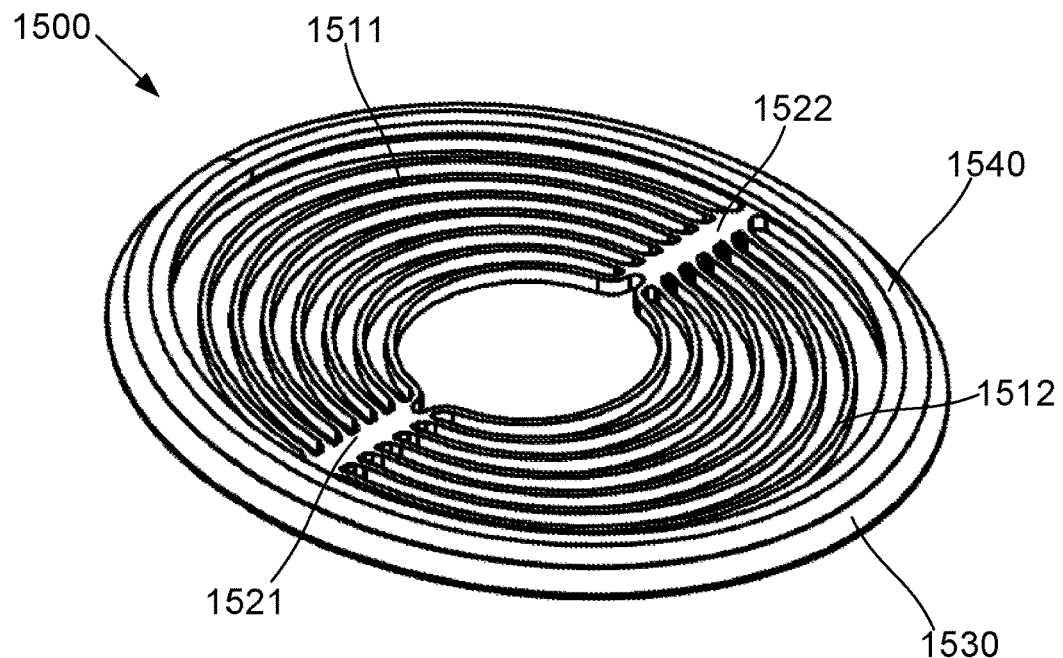
FIG. 15A is a schematic perspective view of a further example of apparatus for opening/closing a tissue opening.
Figure 15B:
FIG. 15B is a schematic cross sectional view of the apparatus of FIG. 15A.
Figure 15C:
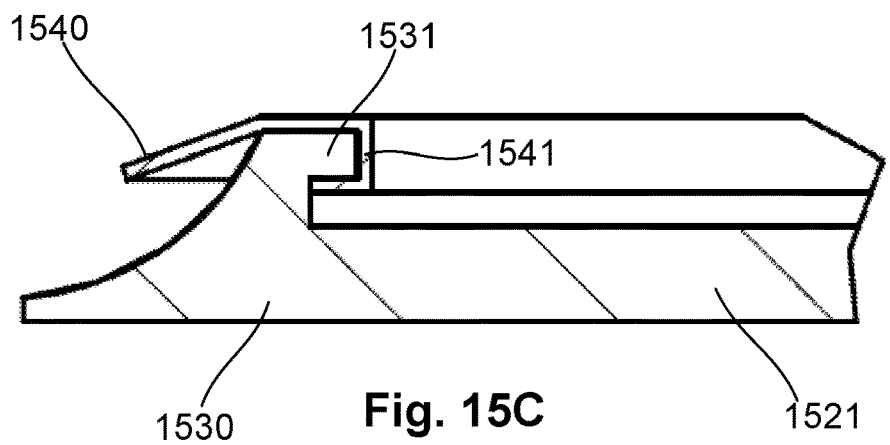
FIG. 15C is a schematic close up cross sectional view of the drive ring coupling of the apparatus of FIG. 15A.

In the above described example of FIGS. 12A to 12H, the drive ring 1240 is mounted inwardly of the frame 1230. However, this is not essential and other arrangements could be used. For example, in the arrangement of FIGS. 15A to 15C, the drive ring is mounted partially within the frame.

In this example, the apparatus 1500 includes two parts, namely the plastic body, including the frame 1530 and arms 1511, 1512 coupled to the frame 1530 via respective arm end portions 1521, 1522, and the drive ring 1540. It will therefore be appreciated that this example is broadly similar to the apparatus 1200 described above, and this will not therefore be described in detail.

In this example however, the drive ring 1540 has a cross sectional shape defining a hooked inner circumferential edge that engages an underside of a lip 1531 extending circumferentially around an inner perimeter of the frame 1530. This allow the drive ring to extend over an upper surface of the frame 1530, so that at least part of the drive ring 1540 is located radially outwardly of the lip 1531. This reduces the volume of the drive ring within the body, allowing a greater area for accommodating tools or a membrane (as will be described in more detail below) whilst maintaining radial rigidity of the drive ring 1540. This also allows the lip 1531 and hooked edge 1541 to function as a ring coupling so that the drive ring 1540 and frame 1530 positively engage, which in turn prevents inadvertent decoupling of the drive ring 1540.

A further example will now be described with reference to FIGS. 16A to 16E, in which the drive ring is mounted externally to the frame.

In this example, the apparatus 1600 includes two parts, namely the plastic body 1610, including the frame 1630 and arms 1611, 1612 coupled to the frame 1630 via respective arm end portions 1621, 1622, and the drive ring 1640. It will therefore be appreciated that this example is broadly similar to the apparatus 1200 described above, and this will not therefore be described in detail.

In this example however, the drive ring 1640 is mounted outwardly of the frame, with the drive ring 1640 being coupled to the 1630 via a tongue and groove arrangement. In particular, the frame 1630 includes a T-shaped tongue 1631 projecting radially outwardly from an outer circumferential perimeter edge of the frame 1631. The drive ring 1641 is formed from first and second drive ring portions 1641, 1642 that corporate to define a groove that receives the tongue 1631. The drive ring portions 1641, 1642 can be coupled via any suitable mechanism, but in one example this is achieved using a swage chamfer that provides an interference fit.

Positioning the drive ring 1640 outwardly of the frame reduces the volume of the drive ring within the body, allowing a greater area for accommodating tools or a membrane (as will be described in more detail below) whilst maintaining radial rigidity of the drive ring 1640. Additionally, this allows the body 1610 and drive ring 1640 to have a reduced height compared to other arrangements. For example the drive ring 1640 could be formed from steel having a 2 mm thickness, with the frame 1630 being made of plastic having a similar thickness. This allows the apparatus to have a greater flexibility in directions perpendicular to the plane defined by the apparatus 1600, whilst maintaining radial rigidity. This allows the apparatus 1600 to flex to conform to the shape of the subject, whilst still maintaining sufficient rigidity in the radial direction to apply the desired forces to the wound.

Additionally, in the current example, the tongue and groove ring coupling prevents inadvertent decoupling of the drive ring 1640, so that the arms 1611, 1612 will be retained in a desired configuration, even if the apparatus flexes.

Figure 17A:
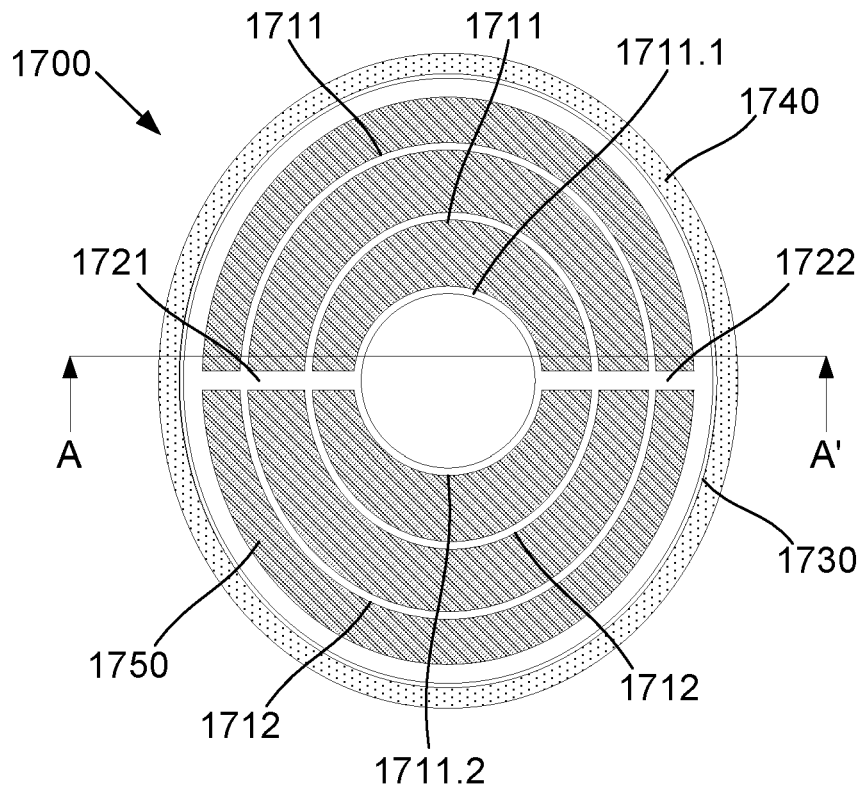
FIG. 17A is a schematic plan view of a further example of apparatus for opening/closing a tissue opening.
Figure 17B:
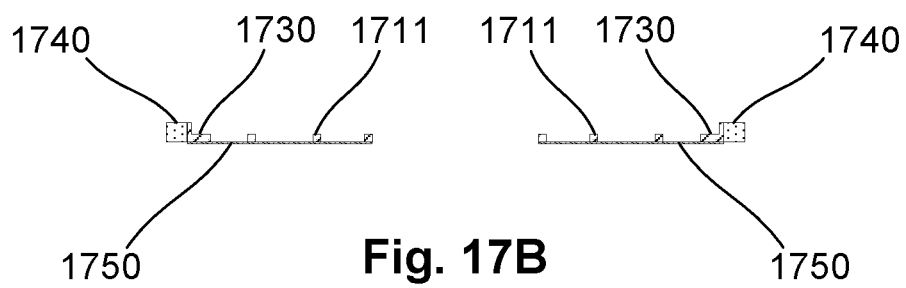
FIG. 17B is a schematic perspective cut-away view of a first variant of the apparatus of FIG. 17A.
Figure 17C:
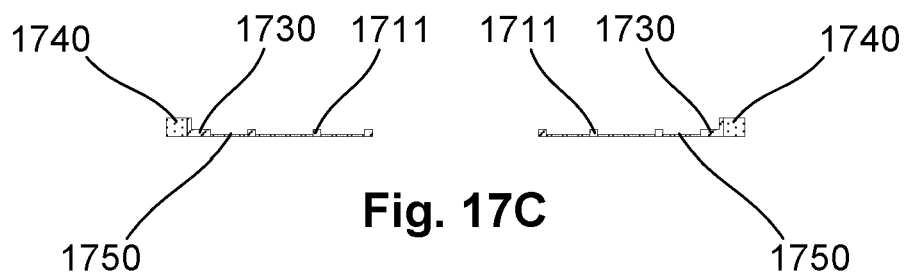
FIG. 17C is a schematic perspective cut-away view of a second variant of the apparatus of FIG. 17A.

A further example will now be described with reference to FIGS. 17A to 17C.

In this example, the apparatus 1700 includes two parts, namely the plastic body, including the frame 1730 and arms 1711, 1712, 1711.1, 1712.1 coupled to the frame 1730 via respective arm end portions 1721, 1722, and the drive ring 1740. In this example, the drive ring is mounted radially outwardly of the frame 1730, although this is not essential. In any event, it will therefore be appreciated that this example is broadly similar to the apparatus arrangements described above, and this will not therefore be described in detail.

In this example, a membrane 1750 is provided that extends between the first arms 1711 and between the second arms 1712. The membrane can be coupled to the arms, for example by being mounted on an underside of the apparatus, as shown for example in FIG. 17B. Alternatively, the membrane could be integrally formed with the arms, for example by having the arms embedded therein, by forming the arms by thickening or ribbing of the membrane, or could be mounted in spaces between the arms 1711, 1712, and this will depend on the preferred implementation and manufacturing techniques.

Irrespective, the membrane 1750 provides an increased contact area for coupling the apparatus 1700 to the subject, and can therefore assist in ensuring the apparatus is retained in position. This also allows a lower strength adhesive to be used to attach the apparatus to the subject, than if attachment is via the arms directly. It will be appreciated from this, that the membrane could be used in any of the above described example configurations.

The membrane can be made of any suitable material, such as a breathable and semi-permeable biologically inert material. In one example, the membrane is made of liquid silicone rubber or the like, although other suitable materials, such as woven or non-woven fabrics, or the like could be used. Additionally, in one example, the membrane can be partially elasticated to facilitate resilience and/or biasing of the apparatus into a particular configuration, as well as to assist distributing tension/compression of the tissue surface within the confines of the frame 1730. In this regard, it will be appreciated that the membrane could in part replace the functionality of the arms 1711, 1712 to distribute forces through the tissue surface, in which case, arms could be partially and/or entirely replaced by the membrane.

Figure 17D:
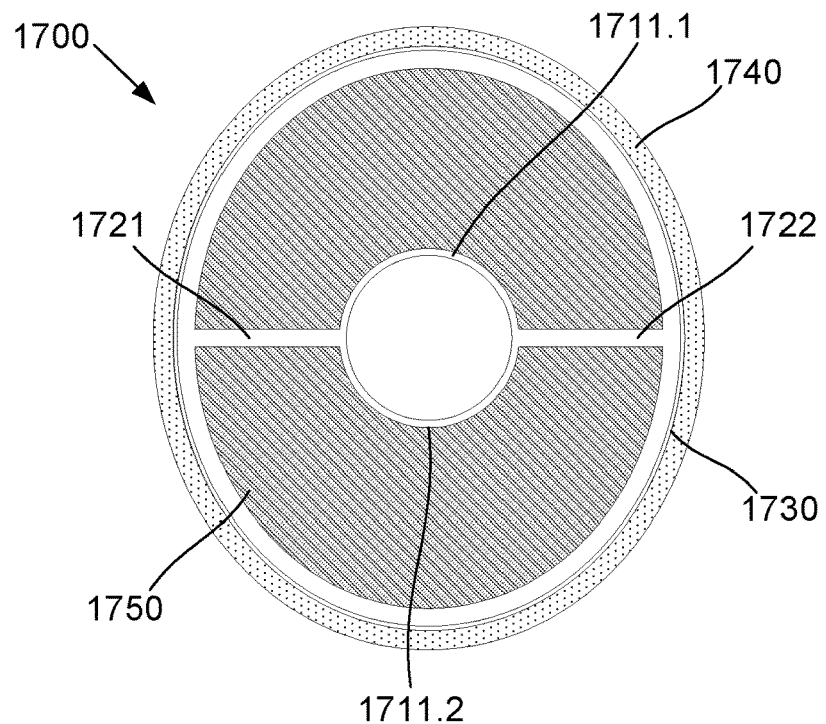
FIG. 17D is a schematic plan view of a first modified version of the apparatus of FIG. 17A.
Figure 17E:
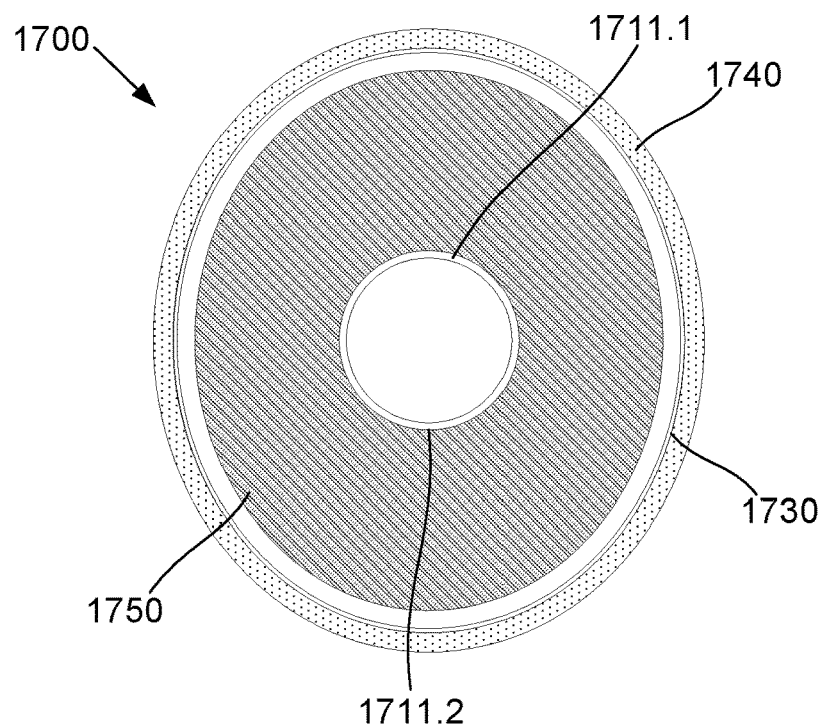

Examples of this are shown in FIGS. 17D and 17E.

In the example of FIG. 17D, the arms 1711, 1712 are removed, leaving only the inner arms 1711.1, 1712.1 coupled to the frame 1730 by the arm end portions 1721, 1722. In this instance, the membrane 1750 extends between the frame 1730 and the inner arms 1711.1, 1712.1 so as to replace the function of the arms 1711, 1712 to distribute forces in the tissue surface.

In the example of FIG. 17E, the arm end portions 1721, 1722 are also removed, so that the inner arms 1711.1, 1712.1 are coupled to the frame 1730 by the membrane 1750 only. It will be appreciated that in this example, the inner arms 1711.1, 1712.1 could be manufactured physically separate to the frame 1730, and in one particular example are formed by ribbing or thickening of the membrane 1750.

Figure 18A:
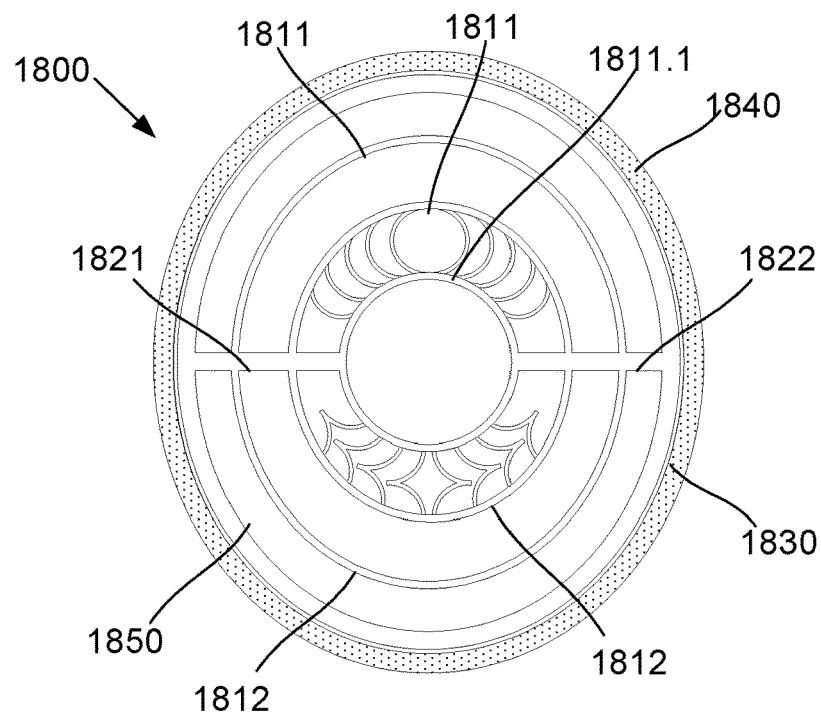
FIG. 18A is a schematic plan view of a further example of apparatus for opening/closing a tissue opening.
Figure 18B:
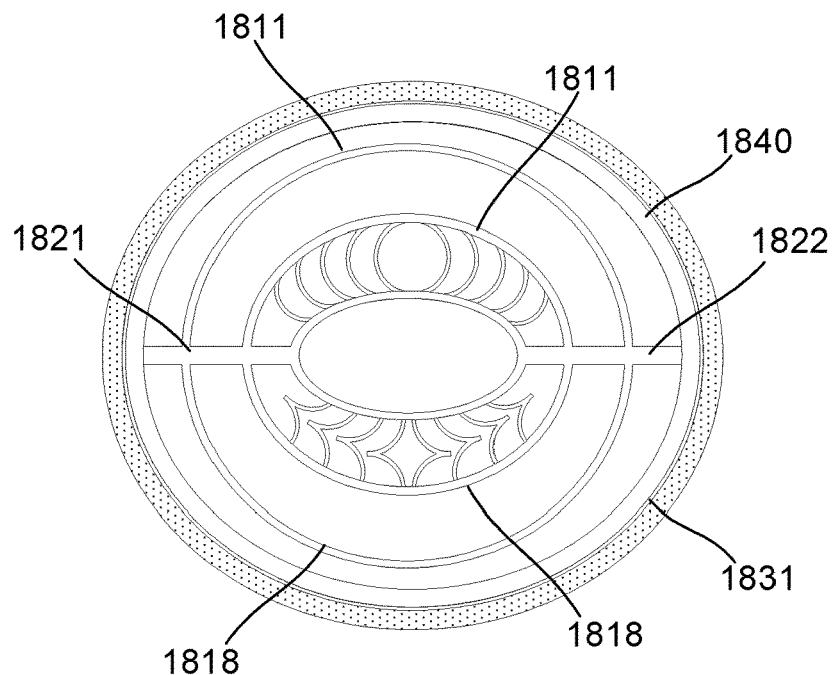
FIG. 18B is a schematic plan view of the apparatus of FIG. 18A.
Figure 19B:
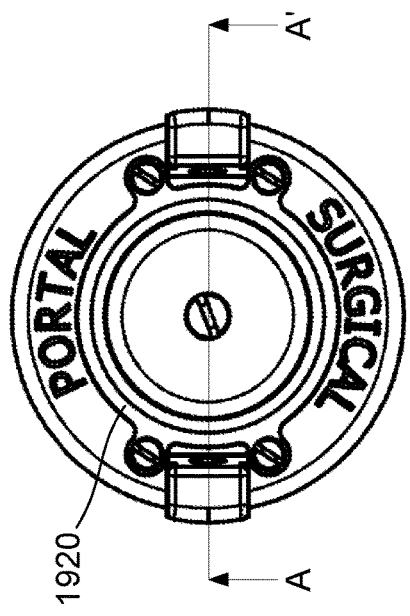
FIG. 19B is a schematic plan view of the incision tool of FIG. 19A.
Figure 19D:
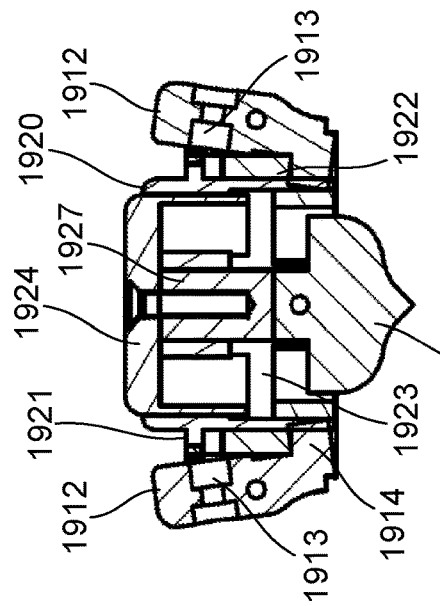
FIG. 19A is a schematic side view of an example of an incision tool.
FIG. 19C is a schematic perspective cut away view of the incision tool along the line A-A' of FIG. 19B; and, FIG. 19D is a schematic cross sectional view of the incision tool along the line A-A' of FIG. 19B.
Figure 19A:
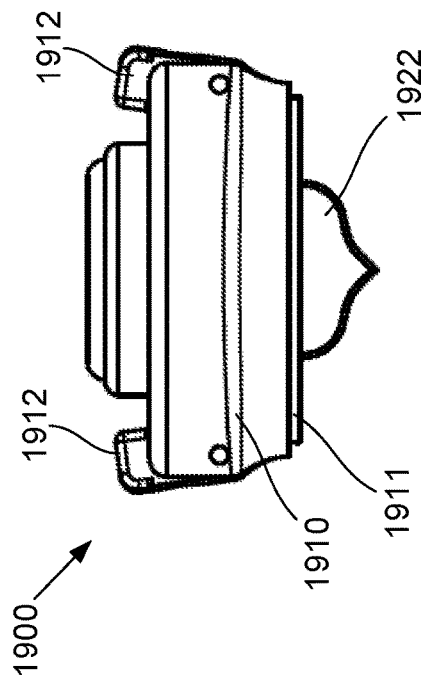
Figure 19C:
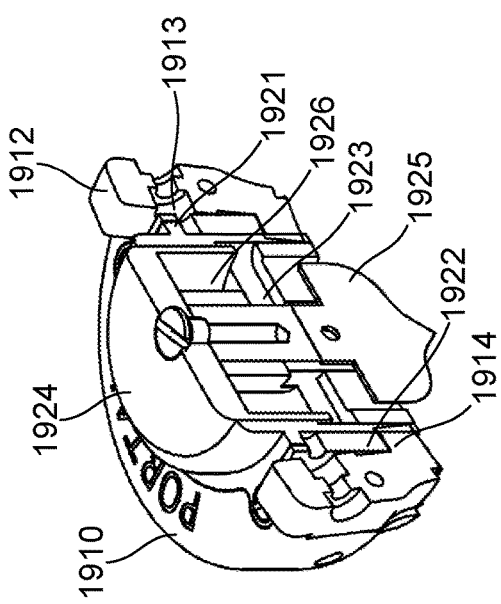

In addition to, or as an alternative to the use of the membrane, ribbing can be provided between the arms and example of this will now be described with reference to FIGS. 18A and 18B.

In this example, the apparatus 1800 includes a plastic body, including the frame 1830 and arms 1811, 1812, 1811.1, 1812.1 coupled to the frame 1830 via respective arm end portions 1821, 1822, and the drive ring 1840. In this example, ribs 1813, 1814 are interspersed between the arms 1811, 1811.1 and 1812, 1812.1, respectively. The ribs extend between adjacent arms, and are adapted to deform as the apparatus and arms deform, thereby accommodating changes in shape of the arm. To achieve this, the ribs typically are curved and/or angled, and two example configurations are shown between the arms 1811, 1811.1 and the arms 1812, 1812.1, respectively. However, it will be appreciated that these configurations are for the purpose of illustration only and are not intended to be limited.

The ribs serve one or more of two main purposes, including providing additional strength to the arms, allowing greater forces to be accommodate, as well as increasing the contact surface area of the device, increasing the ability of the device to adhere to the tissue surface.

Although ribs are shown between two adjacent arms only, it will be appreciated that this is for the purpose of example, and in practice, ribs could be provided between any pair of adjacent arms.

An example incision tool for creating a surgical incision will now be described with reference to FIGS. 19A to 19D.

In this example, the incision tool includes a tool holder having a generally cylindrical body 1910, including a shoulder 1911 defining a key for engaging the drive ring of the tissue opening/closing apparatus, such as the apparatus 1200. In this regard, in this example, the shoulder 1911 is adapted to couple to a drive ring 1240 mounted radially inwardly of a frame 1230, but it will be appreciated that alternative configurations can be provided for outwardly mounted drive rings, such as those described with respect to FIGS. 16A to 16E.

The tool holder can be used to accommodate a range of different tools and includes catches 1912 pivotally mounted to the tool holder body 1910, allowing the different tools to be connected thereto. The catches 1219 are generally L-shaped, including a catch recess 1913 and catch foot 1914, which face inwardly into a tubular opening defined by the tool holder body 1910.

The arrangement further includes the incision tool, which in this example includes a hollow tubular tool body 1920, including a flange 1921 extending circumferentially around the tool holder body 1920, for engaging the catch recess, and a lower edge 1922 for engaging the catch foot 1922. The tool body 1920 also includes an internal spring plate 1923, for supporting a spring within the tool body. A button 1924 is mounted within the tool body 1920 so as to define an internal cavity 1926 between the spring plate 1923 and button 824, which in use contains a spring (not shown). A button shaft 1927 connects the button to a blade 1925.

In use, the button 1924 and blade 1925 are mounted within the tool body 1920 and coupled together. The tool body 1920 is then inserted into the tool holder body 1910, until the lower edge 1922 abuts against the catch feet 1914, causing the buttons to pivot, so that the catch recesses 1913 engage the flange 1921, retaining the tool body 1920 in place.

Once this has been completed, the tool holder can be coupled to a tissue opening/closing apparatus, such as the apparatus 1200, and the button 1924 depressed. This compresses the spring causing the blade 1925 to project through the apparatus and create an incision in the subject between the first and second arms 1211, 1212. Releasing the button 1924 allows the blade to retract under action of the spring. Following this, the tool body 1920 can be removed and the tool holder used to rotate the drive ring 1240, and hence control the degree of opening of the incision.

It will be appreciated that the above described arrangements could be used for other similar tool configuration. Thus, tools can include a tool holder including a tool holder body defining an opening and a tool body that in use is positioned at least partially within the tool holder body. In this case, the tool holder body can engage the drive ring, thereby forming an actuator for rotating the drive ring, whilst allowing different tools to be accommodated therein as required.

For example, when performing surgery, a surgeon could initially use a cutting tool to create the incision. The cutting tool would typically include a blade and button movably mounted to the tool body to allow the blade to be deployed upon depression of the button. Once this has been completed, the cutting tool can be removed, for example by releasing the catches, allowing an optical system to be coupled to the tool holder. This allows the incision to be opened in a controllable manner, whilst being viewed by the surgeon. After this, surgery can be performed using relevant tools such as a trocar system, before the optical system is again used whilst closing the incision by rotating the drive ring using the tool holder. Accordingly, it will be appreciated that this can provide a complete surgical system for creating, opening, using and closing an incision.

The above described arrangements can be used in a wide variety of circumstances and it will be appreciated that different configurations could be provided for different applications. For example, the length and spacing of the arms could be of different sizes to suit a range of different tissue openings. Additionally, different shapes could be used for different applications and the above examples are not therefore intended to be limiting.

The term subject includes any living system, and in particular can include human, or non-human subjects. Thus, whilst the above examples have focussed on a subject such as a human, it will be appreciated that the apparatus and techniques described above can be used with any animal, including but not limited to, primates, livestock, performance animals, such as race horses, or the like.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. Apparatus for opening or closing a tissue opening in a biological subject, the apparatus comprising:

a) at least two flexible arms coupled to a tissue surface in use, each arm being curved outwardly in a mid-portion to accommodate a tissue opening therebetween, the at least two flexible arms being coupled to a frame;
b) a biasing mechanism comprising a drive ring configured to engage the frame, the biasing mechanism being configured to selectively bias opposing ends of each arm to thereby at least one of:
   i) bias mid-portions of the arms apart to assist in at least partially opening the tissue opening; and,
   ii) bias mid-portions of the arms towards each other to assist in at least partially closing the tissue opening.

2. Apparatus according to claim 1, wherein the at least two arms are provided laterally on either side of the tissue opening and wherein the biasing mechanism biases ends of the arms longitudinally relative to the opening and wherein the biasing mechanism moves ends of the arms:
   a) together so as to increase curvature of the arms to thereby bias mid-portions of the arms apart to assist in at least partially opening the tissue opening; and
   b) apart so as to at least partially straighten the arms to thereby bias mid-portions of the arms towards each other to assist in at least partially closing the tissue opening.

3. Apparatus according to claim 1, wherein the apparatus comprises a plurality of laterally spaced first arms on a first side of the tissue opening and a plurality of laterally spaced second arms on a second side of the tissue opening.

4. Apparatus according to claim 3, wherein at least one of:
   a) mid-portions of the first and second arms are curved outwardly in an unbiased state, and wherein the radius of curvature is greater for arms further away from the tissue opening;
   b) first and second arms further away from the tissue opening have a greater length;
   c) mid-portions of the arms are spaced further apart away from the tissue opening; and,
   d) adjusting a separation of the opposing ends of each arm causes a progressively smaller degree of lateral movement of the mid portion a greater distance away from the tissue opening to thereby distribute tension through the tissue surface.

5. Apparatus according to claim 1, wherein the apparatus comprises a membrane extending between at least some of the first arms and between at least some of the second arms and wherein at least one of:
   a) the arms are at least one of:
      i) coupled to the membrane; and,
      ii) integrally formed with the membrane; and
   b) the membrane provides a contact surface for coupling the apparatus to the subject.

6. Apparatus according to claim 1, wherein the biasing mechanism at least partially deforms the frame to thereby bias opposing ends of each arm.

7. Apparatus according to claim 6, wherein the frame and drive ring are configured to deform the frame upon relative rotation of the frame and drive ring.

8. Apparatus according to claim 7, wherein at least one of:
   a) the frame is elastically deformable;
   b) a degree of rotation adjusts an amount of biasing of the arms;
   c) the drive ring and frame are complementarily shaped;
   d) the drive ring and frame are elliptical;
   e) the drive ring is mounted at least one of:
      i) inwardly of the frame; and
      ii) outwardly of the frame;
   f) the frame includes a lip extending circumferentially around at least part of a perimeter of the frame and wherein the drive ring engages the lip; and,
   g) at least one of the frame and a drive ring at least partially immobilize tissue within a perimeter of the frame.

9. Apparatus according to claim 7, wherein the apparatus comprises an actuator including a key coupled to a handle, and wherein in use the key engages the drive ring so that rotation of the handle causes corresponding rotation of the drive ring relative to the frame.

10. Apparatus according to claim 7, wherein, in use, at least one tool can be selectively coupled to the drive ring to thereby support the at least one tool relative to the apparatus and wherein, the tool includes at least one of:
   a) an optical system for viewing the tissue opening;
   b) a blade for creating an incision;
   c) a guide for guiding a surgical instrument;
   d) a tool holder including a tool holder body defining an opening;
   e) a tool body that in use is positioned at least partially within the tool holder body; and,
   f) a blade and button movably mounted to the tool body to allow the blade to be deployed upon depression of the button.

11. Apparatus according to claim 1, wherein the arms are at least one of:
   a) resilient and are curved in an unbiased state;
   b) resilient;
   c) incompressible;
   d) unstretchable; and,
   e) made of at least one of:
      i) a biocompatible material;
      ii) a core with a biocompatible coating;
      iii) a polymer;
      iv) high density polyethylene;
      v) polypropylene; and
      vi) metal; and
   f) coupled to the frame via respective arm end portions, and wherein each arm is connected to the arm end portion via a live hinge.

12. Apparatus according to claim 1, wherein the coupling mechanism comprises at least one of:
   a) an adhesive surface provided on an underside of the arms;
   b) an adhesive layer provided on an underside of the arms;
   c) a number of projections extending from an underside of the arms, the projections penetrating the tissue surface in use; and,
   d) at least one adhesive patch applied over an upperside of the arms.

13. Apparatus according to claim 1, wherein the biasing mechanism is adjustable to allow closing forces on the tissue opening to be controlled.

14. Apparatus according to claim 1, wherein a first end of each arm is coupled to a first arm end portion and a second end of each arm is coupled of to a second arm end portion and wherein a relative separation of the first and second arm end portions provides the biasing mechanism.

15. Apparatus according to claim 14, wherein the first and second arm end portions are coupled to the tissue surface by at least one of:
   a) an adhesive surface provided on an underside of the arm end portions;
   b) an adhesive layer provided on an underside of the arm end portions;

c) a number of projections extending from an underside of the arm end portions, the projections penetrating the tissue surface in use; and, d) at least one adhesive patch applied over an upperside of the arm end portions.

16. Apparatus according to claim 14, wherein at least one of first and second arm end portions are coupled to a frame and wherein the frame at least one of:
   a) extends around at least part of a perimeter of the apparatus;
   b) surrounds at least part of the arms and arm end portions;
   c) is coupled to the tissue surface;
   d) is coupled to the tissue surface by at least one of:
      i) an adhesive surface provided on an underside of the arm end portions; and
      ii) an adhesive layer provided on an underside of the arm end portions.

17. Apparatus according to claim 16, wherein at least one of:
   a) a first arm end portion is coupled to the frame and a second arm end portion is movable relative to the frame so that movement of the second arm end portion provides the biasing mechanism;
   b) a second arm end portion is selectively secured to the frame using a releasable fastener; and
   c) a threaded member is coupled to the second arm end portion and the frame so that rotation of the threaded member adjusts a separation of the second arm end portion and the frame.

18. Apparatus according to claim 1, wherein at least one of:
   a) the arms have at least one of:
      i) a substantially rectangular cross section; and
      ii) a flattened underside; and
   b) biasing of the arms generates a torsional force in the mid-portions of the arms, and wherein the torsional force results in a downward force on the tissue surface; and,
   c) the arms include projections that extend from an underside of the arms and penetrate the tissue surface in use and wherein at least one of:
      i) the projections are adapted to the deliver a bioactive material into the tissue around the tissue opening; and
      ii) the projections generate a closing force in the dermal layers below the tissue surface thereby closing the tissue opening below the tissue surface.

19. A method of closing a tissue opening in a biological subject, the method comprising:
   a) coupling at least two flexible arms to a tissue surface on either side of the tissue opening with each arm being curved outwardly in a mid-portion to thereby accommodate the tissue opening therebetween;
   b) coupling the at least two flexible arms to a frame; and
   c) biasing opposing ends of each arm apart by deforming the frame with a drive ring to thereby at least partially straighten the arms, which in turn biases the mid-portions towards each other to at least partially close the tissue opening.

20. A method of creating a tissue opening in a biological subject, the method comprising:
   a) coupling at least two flexible arms to a tissue surface, wherein in an unbiased state the arms are resilient and curved in at least a mid-portion;
   b) coupling the at least two flexible arms to a frame;
   c) at least partially biasing opposing ends of each arm apart by deforming the frame with a drive ring so that the arms are at least partially straightened;
   d) creating an incision between the arms; and,
   e) at least partially unbiasing the opposing ends of the arms so that the mid-portions move apart to thereby open the incision and create a tissue opening.

* * * * *